(12) United States Patent
Bluchel et al.

(10) Patent No.: US 11,135,347 B2
(45) Date of Patent: Oct. 5, 2021

(54) DIALYSIS DEVICE AND METHOD OF DIALYSIS

(71) Applicant: TEMASEK POLYTECHNIC, Singapore (SG)

(72) Inventors: Christian Gert Bluchel, Singapore (SG); Liutong Lin, Singapore (SG)

(73) Assignee: Temasek Polytechnic, Singapore (SG)

( * ) Notice: Subject to any disclaimer, the term of this patent is extended or adjusted under 35 U.S.C. 154(b) by 504 days.

(21) Appl. No.: 15/827,341

(22) Filed: Nov. 30, 2017

(65) Prior Publication Data

US 2018/0147338 A1    May 31, 2018

Related U.S. Application Data

(63) Continuation of application No. 13/885,273, filed as application No. PCT/SG2011/000395 on Nov. 8, 2011, now abandoned.

(30) Foreign Application Priority Data

Nov. 15, 2010    (GB) ..................... 1019228

(51) Int. Cl.
    *A61M 1/28*    (2006.01)
    *A61M 1/16*    (2006.01)

(52) U.S. Cl.
    CPC .......... *A61M 1/28* (2013.01); *A61M 1/1696* (2013.01); *A61M 1/1658* (2013.01);
    (Continued)

(58) Field of Classification Search
    CPC ........ A61M 1/28; A61M 1/284; A61M 1/287; A61M 1/1696; A61M 1/1658;
    (Continued)

(56) References Cited

U.S. PATENT DOCUMENTS

4,552,552 A * 11/1985 Polaschegg ............ A61M 1/30
                                                    210/416.1
4,661,246 A    4/1987 Ash
(Continued)

FOREIGN PATENT DOCUMENTS

AU    2011329576 B2    12/2015
CN    103209721 B      11/2016
(Continued)

OTHER PUBLICATIONS

Australian Patent Examination Report No. 1 for AU 2011329576, dated Jun. 4, 2014, 3 pages.
(Continued)

*Primary Examiner* — Tiffany Legette
(74) *Attorney, Agent, or Firm* — Eric D. Babych; Barnes & Thornburg LLP

(57) ABSTRACT

The present disclosure relates to dialysis devices. In some embodiments, a dialysis device may include a disposable housing having a storage chamber in fluid communication with a dialysate flow path. Also included may be a controller, an interface capable of operably coupling the controller and the disposable housing, a fluid displacement structure, a pump configured to actuate a deformable diaphragm, and a pressure sensor to trigger the reversal of the pump. The flow path may be fluidly sealed from the controller and the interface.

19 Claims, 29 Drawing Sheets

(52) U.S. Cl.
CPC . *A61M 2205/121* (2013.01); *A61M 2205/123* (2013.01); *A61M 2205/126* (2013.01); *A61M 2205/128* (2013.01); *A61M 2205/33* (2013.01); *A61M 2205/7518* (2013.01); *A61M 2209/088* (2013.01)

(58) Field of Classification Search
CPC ...... A61M 2205/121; A61M 2205/123; A61M 2205/126; A61M 2205/128; A61M 2205/33; A61M 2205/7518; A61M 2205/7527; A61M 1/14; A61M 1/16; A61M 2205/8206
See application file for complete search history.

(56) References Cited

U.S. PATENT DOCUMENTS

| | | | |
|---|---|---|---|
| 4,684,460 A | 8/1987 | Issautier | |
| 2003/0009123 A1* | 1/2003 | Brugger | A61M 1/3656 604/4.01 |
| 2004/0019312 A1* | 1/2004 | Childers | A61M 1/288 604/4.01 |
| 2007/0179431 A1* | 8/2007 | Roberts | A61M 1/1696 604/29 |
| 2008/0132828 A1 | 6/2008 | Howard | |
| 2010/0114012 A1 | 5/2010 | Sandford et al. | |
| 2010/0130920 A1* | 5/2010 | Lo | A61M 39/20 604/29 |
| 2010/0204765 A1* | 8/2010 | Hall | A61M 1/28 607/105 |
| 2011/0071465 A1* | 3/2011 | Wang | G16H 20/40 604/67 |
| 2011/0184340 A1* | 7/2011 | Tan | B01D 15/362 604/29 |

FOREIGN PATENT DOCUMENTS

| | | | |
|---|---|---|---|
| EP | 0152717 | A1 | 8/1985 |
| HK | 1187560 | B | 1/2018 |
| JP | S61119275 | A | 6/1986 |
| JP | 2009525071 | A | 7/2009 |
| JP | 2011509801 | A | 3/2011 |
| JP | 2011525404 | A | 9/2011 |
| JP | 5681294 | B2 | 1/2015 |
| NZ | 609385 | | 8/2014 |
| TW | I577397 | B | 4/2017 |
| WO | 2009094182 | A2 | 7/2009 |
| WO | 2009157878 | A1 | 12/2009 |

OTHER PUBLICATIONS

Chinese Office Action for CN 201180054932.9, dated Dec. 29, 2014, no translation, 6 pages.
Chinese Office Action for CN 201180054932.9, dated Oct. 26, 2015, machine translation, 5 pages.
Chinese Office Action for CN 201180054932.9, dated Apr. 19, 2016, machine translation, 5 pages.
European Extended Search Report for EP 11841543.9, dated Feb. 27, 2018, 11 pages.
European Office Action for EP 11841543.9, dated Oct. 29, 2019, 5 pages.
European Office Action for EP 11841543.9, dated Sep. 7, 2020, 4 pages.
Indian First Examination Report for IN 3750/DELNP/2013, dated Jan. 29, 2019, 7 pages.
Japanese Search Report for JP 2013538691, dated Mar. 31, 2014, machine translation, 25 pages.
Japanese Office Action for JP 2013538691, dated May 7, 2014, machine translation, 2 pages.
Japanese Office Action for JP 2013538691, dated Aug. 27, 2014, 6 pages.
New Zealand First Examination Report for NZ 609385, dated Nov. 28, 2013, 2 pages.
PCT International Search Report for PCT/SG2011/000395, dated Dec. 23, 2011, 4 pages.
PCT Written Opinion for PCT/SG2011/000395, dated Dec. 23, 2011, 5 pages.
PCT International Preliminary Report on Patentability for PCT/SG2011/000395, completed Oct. 10, 2012, 32 pages.
Taiwan Office Action for TW 100140799, dated Oct. 15, 2015, 2 pages.
United States Final Office Action for U.S. Appl. No. 13/885,273, dated Aug. 30, 2017, 28 pages.

* cited by examiner

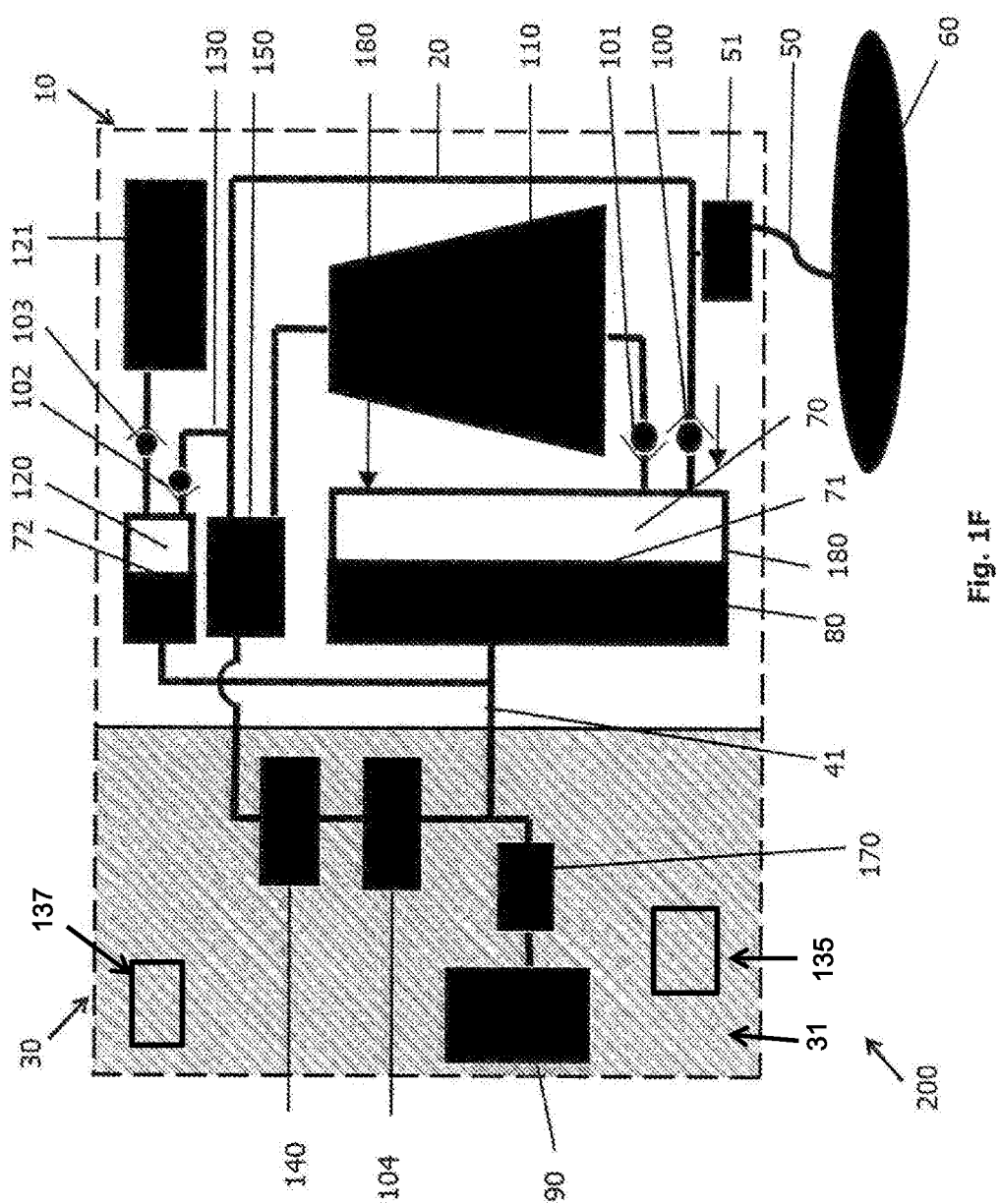

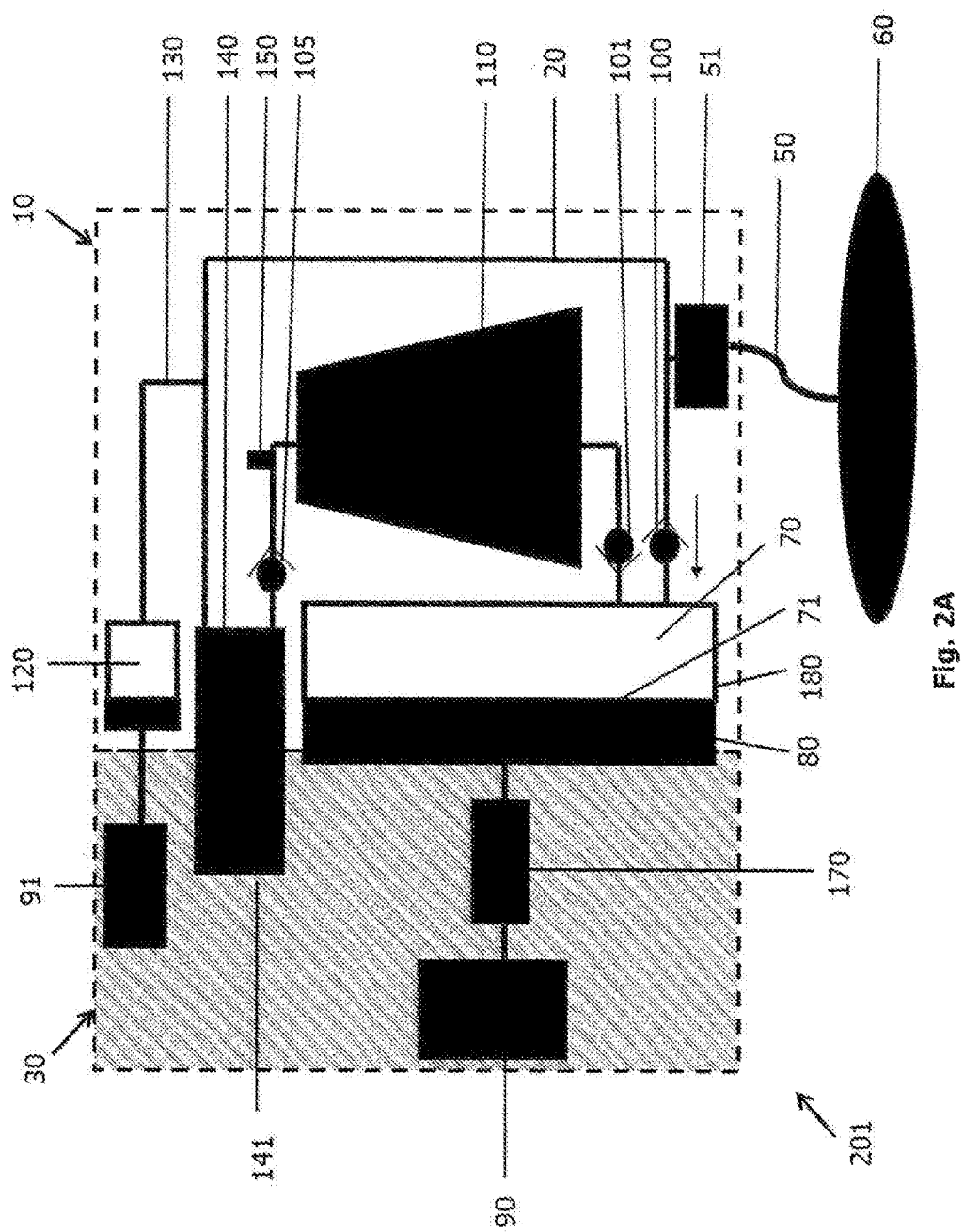

511

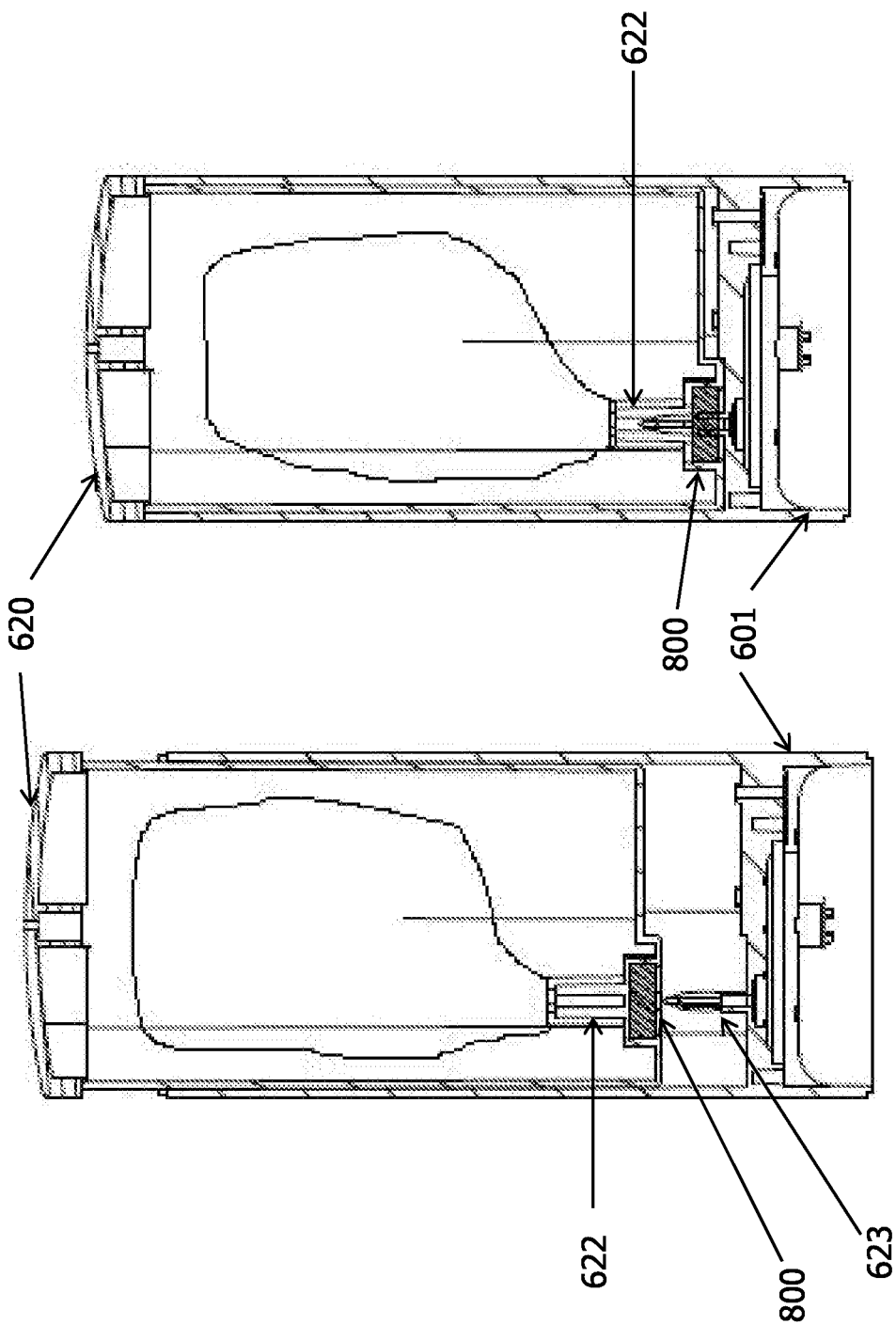

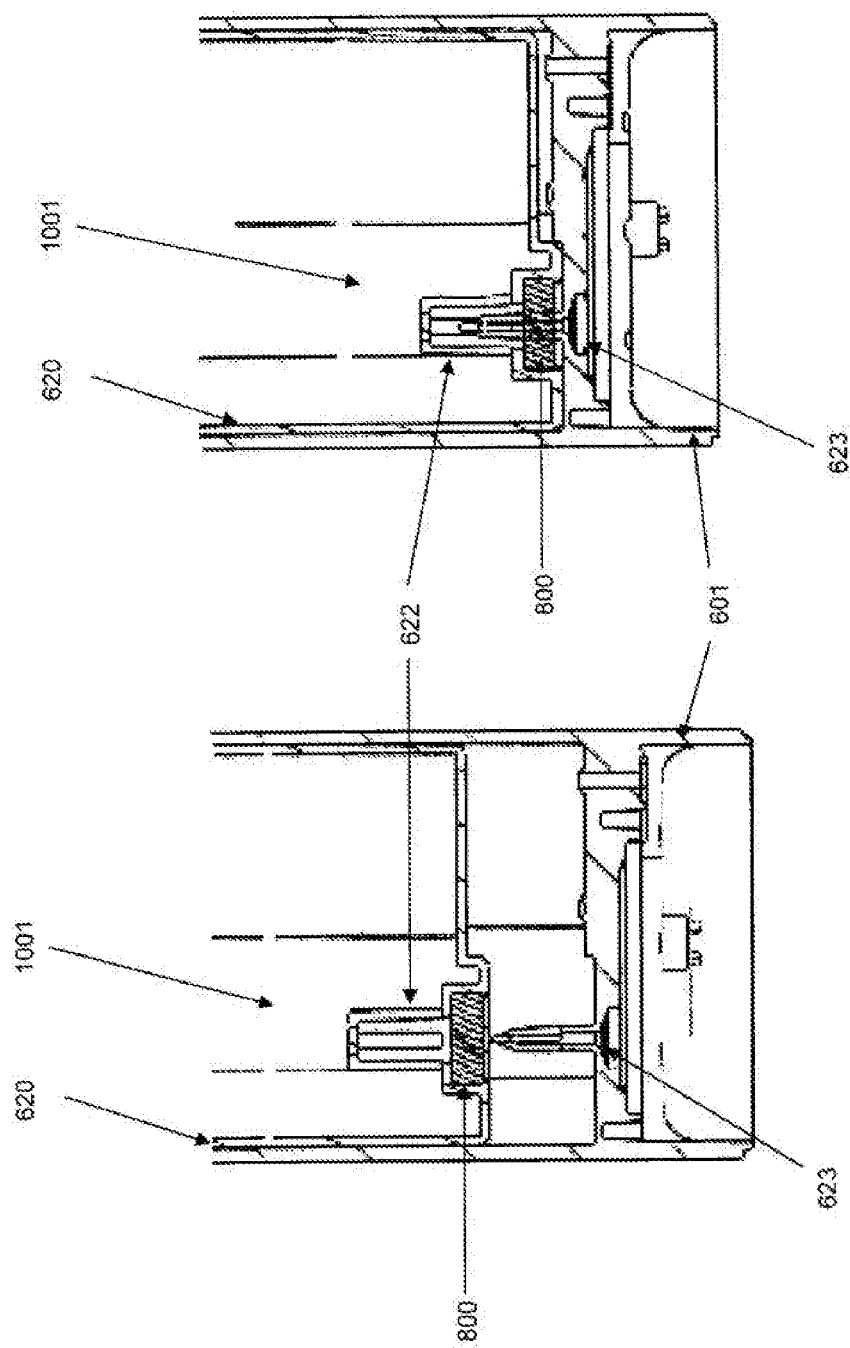

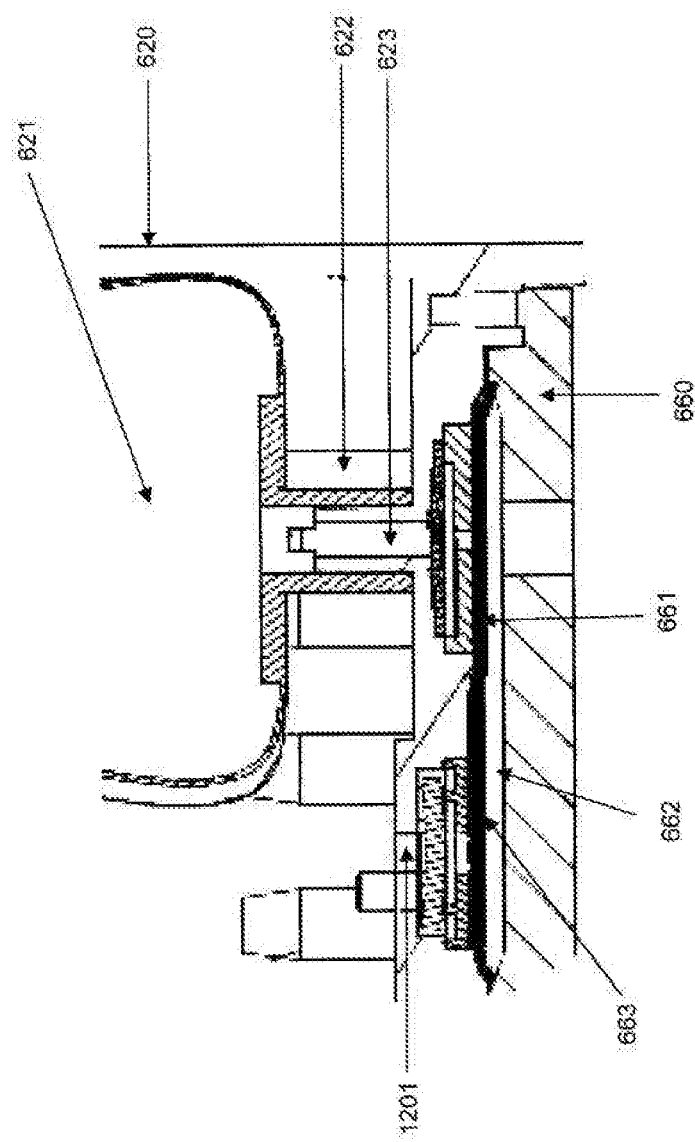

DIALYSIS DEVICE AND METHOD OF DIALYSIS

TECHNICAL FIELD

The present invention relates to a dialysis device and in particular to a portable or wearable dialysis device. The invention also relates to a method of conducting dialysis.

BACKGROUND

Kidneys are vital organs of the human homeostasis system. Kidneys act as a natural filter in the body which remove toxic metabolic wastes such as urea from the blood. Kidney failure or malfunction may lead to an accumulation of toxins and to an imbalanced electrolyte level in the blood, which may result in undesirable repercussions that are hazardous to an individual's health.

Renal dysfunction and/or failure and, in particular, end-stage renal disease, may cause the body to lose the ability to adequately remove toxic waste in the blood and restore the optimal level of electrolytes in the blood, within physiological ranges. Dialysis is commonly used to replace inadequate kidney function by removing toxic waste.

For the past few years, the predominant form of dialysis used for patients with end-stage renal disease (ESRD) is hemodialysis. Hemodialysis involves the use of an extracorporeal system for the removal of toxins directly from the patient's blood by passing a large amount of the patient's blood through a filtering unit or dialyzer. Hemodialysis treatment typically lasts several hours and must be performed under medical supervision three to four times a week, which significantly decrease a patient's mobility and quality of life. Furthermore, as hemodialysis is performed periodically rather than on a continuous basis, patient health deteriorates as soon as a "treatment cycle" in which contaminants are removed has been completed.

The other form of dialysis used for patients with kidney failure is peritoneal dialysis, most commonly applied in the following two techniques: "continuous ambulatory peritoneal dialysis" (CAPD) and "automated peritoneal dialysis" (APD). In CAPD, fresh dialysate is infused into the patient's abdominal (peritoneal) cavity where, by means of diffusion, metabolic waste and electrolytes in the blood are exchanged with the dialysate across the peritoneal membrane. To allow sufficient diffusion of the electrolytes and metabolic waste to occur, the dialysate is retained in the abdominal (peritoneal) cavity for a couple of hours before removal and replacement (of the spent dialysate) with fresh dialysate. Major drawbacks of continuous ambulatory peritoneal dialysis are a low level of toxin clearance, and the need to continuously replace the spent dialysate, which can be arduous for the patient and disruptive to his/her daily activities.

To address this problem, devices have been designed that reconstitute used/spent dialysate from hemodialysis and/or peritoneal dialysis as opposed to discarding it. However, current devices that reconstitute used/spent dialysate have several associated disadvantages including complex set up procedures and difficulties in maintaining the sterility of components. A further disadvantage is that current devices often require a plurality of fluid connections, which increases the risk of introducing biological contamination and reduces sterility of the device. In addition several components must be disposed of either daily, weekly or monthly adding another layer of complexity to the operation of such devices. In addition, the flow system of known regenerating dialysis devices requires a plurality of pumps, which in turn undesirably increases the overall size, weight and power consumption of the device.

Accordingly, there is a need to provide a dialysis device that overcomes or at least ameliorates one or more of the disadvantages described above. There is also a need to provide a dialysis device without compromising on the size, weight and power consumption of the device.

SUMMARY

According to a first aspect, there is provided a dialysis device comprising:

a disposable housing having a flow path along which dialysate received from a patient is subjected to contaminant removal when in operation;

a controller for controlling the operation of said disposable housing; and an interface structure capable of operably coupling the controller and the disposable housing to enable the removal of contaminant from the dialysate;

wherein the flow path is fluidly sealed from the controller and interface.

Advantageously, the disposable housing may be disposed of on a daily basis or after each dialysis cycle. This is advantageous as this improves the sterility of the disposable housing and reduces the chances of patient infection. It is a further advantage of the device that as the flow path is fluidly sealed from the controller, the sterility of the device can be maintained by daily disposal of disposable housing and therefore the disclosed device does not suffer, or is at least not as readily prone to, biological contamination compared to known dialysis devices.

It is a further advantage of the dialysis device that a single connector between the disposable housing and controller is required, thus reducing the complexity of setting the device up for operation.

It is a further advantage that the connector between the disposable housing and the controller is fluidly sealed to prevent biological or chemical contamination of the device.

It is a further advantage that the size of the dialysis device according to the disclosure can be significantly reduced relative to other dialysis devices.

It is a further advantage that the dialysis device according to the disclosure operates at a low system pressure resulting which in turn improves energy utilisation.

It is a further advantage that the device according to the disclosure is energy efficient.

According to a second aspect, there is provided a dialysis controller operable with a disposable housing having fluid displacement means configured to move dialysate along a flow path disposed within said housing, the controller comprising:

actuation means for actuating said fluid displacement means and an interface for connecting said controller to said disposable housing, wherein said controller and said interface are fluidly sealed from said flow path during operation of the disposable housing.

According to a third aspect, there is provided a disposable dialysis housing that is configured to be operated by a controller, the disposable housing comprising:

a flow path disposed therein along which dialysate received from a patient is subjected to contaminant removal when in operation; and an interface for connecting said housing to a corresponding interface of said controller, wherein in use, the flow path is fluidly sealed from said controller and said interface.

According to a fourth aspect, there is provided a dialysis system comprising:

a disposable housing having a flow path containing dialysate received from a patient, the dialysate undergoing contaminant removal while disposed in the flow path;

a controller operably connected to said disposable housing by an interface to control the operations of the disposable housing;

wherein said flow path is fluidly sealed from the controller and interface.

According to a fifth aspect, there is provided use of a dialysis device in accordance with the present disclosure, to treat a patient suffering from kidney malfunction.

According to a sixth aspect, there is provided a dialysis method implemented in a dialysis system comprising a disposable housing having a flow path extending therethrough and a sorbent zone for contaminant removal, an interface operably coupling said disposable housing to a controller for controlling the passage of dialysate along the flow path of said disposable housing, the method comprising the step of:

passing a dialysate along the flow path of said disposable housing while ensuring that the flow path and dialysate therein is fluidly sealed from the interface and the controller.

According to a seventh aspect, there is provided a dialysis system comprising:

a disposable housing having a flow path containing dialysate received from a patient, the dialysate undergoing contaminant removal while disposed in the flow path;

a pressure sensor configured to determine fluid pressure changes in the flow path.

a controller operably connected to said disposable housing by an interface to control the operations of the disposable housing and wherein the controller is configured to determine the flow rate of dialysate in the flow path based on the pressure changes output by the pressure sensor.

According to a eighth aspect, there is provided a kit comprising the dialysis device according to the first aspect, together with instructions for use.

According to a ninth aspect, there is provided a kit comprising the controller according to the second aspect, together with instructions for use.

According to a tenth aspect, there is provided a kit comprising the disposable housing according to the third aspect, together with instructions for use.

Definitions

The following words and terms used herein shall have the meaning indicated:

The term "sorbent" as used herein broadly refers to a class of materials characterized by their ability to adsorb and/or absorb the desired matter of interest.

The term "non-toxic" as used herein refers to a substance that causes little to no adverse reactions when present in the human body.

The term "contaminants" in the context of this specification, means any constituents, typically toxic constituents, within a dialysate that are generally harmful to human health and which are desirable to be removed in a dialysate detoxification process. Typical contaminants include, but are not limited to ammonium, phosphates, urea, creatinine and uric acid.

The term "biocompatible" as used herein refers to the property of a material that does not cause adverse biological reactions to the human or animal body.

The term "upstream" as used herein refers to a localization within the flow path, relative to a point of reference, and in direction opposite to that of the dialysate flow. The term "downstream" as used herein refers to a localization within the flow path, relative to a point of reference, and in direction of the dialysate flow.

The term "crack-pressure" as used herein refers to the point at which the internal pressure of a pneumatic system triggers the opening of a valve.

The term "regenerate" as used herein refers to the action of detoxifying dialysate by removal of uremic toxins.

The term "reconstitute" as used herein refers to the action of converting regenerated dialysate to essentially the same state and chemical composition as fresh peritoneal dialysate prior to dialysis.

The term "outflow mode" as used herein refers to the flow of dialysate from the patient's body through a sorbent. The flow is referenced from the patient's body.

The term "inflow mode" as used herein refers to the flow of the dialysate from a sorbent to the patient's body. The flow is referenced to the patient's body.

The term "fluid" as used herein refers to a liquid or a gas.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers "within that range, for example, 1, 2, 3, 4, 5, and 6. This applies regardless of the breadth of the range The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

DISCLOSURE OF OPTIONAL EMBODIMENTS

Exemplary, non-limiting embodiments of a flow system of dialysis device will now be disclosed.

The flow system of a dialysis device comprises: a disposable housing having a flow path along which dialysate received from a patient is subjected to contaminant removal;

a controller for controlling the operation of said disposable housing; and an interface capable of connecting the controller and the disposable housing to enable contaminant removal from the dialysate;

wherein the flow path is fluidly sealed from the controller and interface.

In one embodiment, the disposable housing further comprises a sorbent zone in fluid communication with the dialysate flow path for removing contaminants in the dialysate.

In one embodiment, the disposable housing further comprises a storage chamber in fluid communication with the dialysate flow path for storing the dialysate therein.

In one embodiment, the disposable housing further comprises a fluid displacement means providing a fluid displacement structure configured to move the dialysate along the dialysate flow path.

In one embodiment, the disposable housing further comprises valve means disposed along the dialysate flow path configured to control the direction of movement of the dialysate relative to the sorbent zone and storage chamber. In one embodiment, the valve means are operative by the flow direction of dialysate along said flow path. In a preferred embodiment, the valve means are check valves. In another embodiment, the valves are pressure actuated or mechanically actuated. In one embodiment, the controller further comprises actuation means that provides an actuator for actuating said fluid displacement means and said valve means when said controller is connected to the disposable housing by said interface.

In a preferred embodiment, all check-valves along the dialysate flow path to the sorbent zone are resistant to clogging by fibrin.

In a preferred embodiment, the fluid displacement means comprises a deformable diaphragm.

In one embodiment, the deformable diaphragm is in fluid contact on one side with the dialysate flow path, and on another opposite side, in contact with a pressure chamber that is capable of receiving fluid therein. Pressure changes within the pressure chamber deform said deformable diaphragm which thereby moves dialysate within said dialysate flow path.

In one embodiment, the deformable diaphragm is disposed and fluidly sealed from the pressure chamber and a rigid member.

In one embodiment, the actuation means comprises a pump capable of fluid communication with the pressure chamber when said interface operably couples said disposable housing to said controller.

In another embodiment, the actuation means is a motor which drives a piston wherein said piston actuates the deformable diaphragm.

In one embodiment, the pump is selected from the group consisting of gear pumps, diaphragm pumps, piston pumps, hydraulic pumps, pneumatic pumps and mechanical pumps. In a preferred embodiment, the pump is a pneumatic pump. In one embodiment, the pump is capable of achieving a dialysate flow rate of from 0.1 l/hr to 20 l/hr.

In one embodiment, the interface comprises a conduit connector that fluidly couples the pump of the controller to the pressure chamber of the disposable housing.

In one embodiment, the conduit connector comprises a first mating part disposed on the controller and a second mating part disposed on the disposable housing, and wherein the first and second mating parts are configured to lockingly engage with each other.

In one embodiment, the fluid displacement means is integrally formed with a wall of the storage chamber.

This is advantageous as it permits the pumping mechanism of the dialysis device to be shared by the storage chamber thereby permitting a reduction in the size of the disposable housing. This is further advantageous as it permits the construction of a more portable and unobtrusive device to be used by a patient.

In one embodiment, the disposable housing comprises an additive dispensing means for dispensing a desired additive into the dialysate. In one embodiment, the additive dispensing means is activated by fluid pressure changes that occur in the conduit connector that is in fluid communication with the pump.

This is advantageous, as only one pump, and only one interface connector is required to activate both the storage chamber comprising a deformable diaphragm to move dialysate along the flow path and the additive dispensing means. This reduces the requirement for additional pumps and connections and thus results in a significant reduction in the size of the dialysis device relative to known dialysis devices.

In one embodiment, the disposable housing further comprises a gas vent in fluid communication with the flow path for venting gas from said dialysate. In one embodiment, the gas vent is activated by fluid pressure changes that occur in the conduit connector that is in fluid communication with the pump.

Again, this is advantageous, as only one pump is required to activate the storage chamber comprising a deformable diaphragm to move dialysate along the flow path, the additive dispensing means and the gas vent means. As all of these elements of the device can be activated by a single pump and a single connection this further permits miniaturization of the device and enhances portability and energy efficiency. Furthermore, with only one pump to activate these elements there is also a significant reduction in the complexity of the device which results in a decrease in manufacturing costs relative to known dialysis devices.

In one embodiment, the conduit connector is insulated such that there is no electrical contact between the disposable housing and the controller.

It is an advantage of the device according to the disclosure that the conduit connector results in no electric or electronic contact between the disposable housing and controller.

In an alternative embodiment, the interface provides electric or electronic contact between the disposable housing and controller.

In one embodiment, the storage chamber is located upstream of said sorbent zone.

In one embodiment, the controller comprises a computer configured to act on instructions for operation of the pump.

In one embodiment, the interface comprises a pressure sensor configured to determine the pressure of said dialysate when in the disposable housing. In one embodiment, the pressure sensor is disposed in the controller. In one embodiment, the pressure sensor is disposed in the controller and is in fluid communication with the conduit connector. In a preferred embodiment, the pressure sensor is disposed in the interface.

Advantageously, the pressure sensor can, by determining the pressure of the dialysate in the flow path, also determine the pressure in the peritoneal cavity of a patient. This is further advantageous as it permits the use of one sensor to the pressure of the dialysate in the flow path and in the peritoneal cavity of a patient. It is a further advantage that the use of one sensor permits the device to be reduced in size to fewer components being required in the device.

In another embodiment, the disposable housing further comprises a fibrin filter means disposed along the flow path to remove fibrin from dialysate before said dialysate enters said flow path. In one embodiment, the fibrin filter means is disposed immediately adjacent to the patient's body, for example at the exit of the patient's peritoneal cavity. In one embodiment, the filter for removing the fibrin is made of poly (vinyl) chloride (PVC). In one embodiment, the filter for removing the fibrin is made of polypropylene. The filter may also be capable of withstanding the pressure within the flow system without any appreciable change in its desired properties. Advantageously, the fibrin filter means is capable of removing fibrin, mucus or forms of coagulation arising from the peritoneal cavity before the dialysate enters the flow system. This advantageously reduces the risk of clogging of the flow system. More advantageously, filtering off fibrin containing material prolongs the lifespan of the flow system. The fibrin filter means may be a filtration device, a filter paper or any means suitable for filtering away fibrin containing material in the dialysate.

In one embodiment, the flow path may comprise a trap located upstream of the sorbent zone. In one embodiment, the trap comprises an inlet valve and a filter located opposite the inlet valve. The inlet valve is preferably a resiliently deformable disk valve. In use the dialysate enters the trap in an inflow mode through the disk valve. During an outflow mode the disk valve is closed preventing the flow of dialysate from the sorbent zone to the patient. The dialysate that enters the sorbent zone may comprise fibrin. The fibrin is prevented from entering the sorbent zone by the filter and is therefore retained in the trap. Advantageously, the trap is capable of removing fibrin, mucus or forms of coagulation arising from the peritoneal cavity before the dialysate enters the sorbent zone of the dialysis device. This advantageously reduces the risk of clogging of the flow path. More advantageously, filtering off fibrin containing material prolongs the lifespan of the flow system. The filter means may be a filtration device, a filter paper or any means suitable for filtering away fibrin containing material in the dialysate.

In one embodiment, the flow system may further comprise a micro-organism filter means being disposed along said flow path, said micro-organism filter means being configured to remove microorganisms from the dialysate when transmitted along the flow path. In one embodiment, the micro-organism filter means may be a micro-organism filter capable of inactivating bacteria from the dialysate by having bactericidal properties. The filter means also serves to remove any microorganisms that have inadvertently entered the flow system.

As the dialysis device works to regenerate and reconstitute spent dialysate, the presence of a microorganism filter means for filtering microorganisms from the dialysate ensures the sterility of the dialysate returning to the patient's body. In one embodiment, the micro-organism filter means may be a filtration device, a filter membrane or any means suitable for filtering away micro-organisms containing material in the dialysate. In one embodiment, the bacteria filter for removing microorganisms has pore sizes of no more than about 0.20 microns. In another embodiment, the micro-organism filter has a surface area of from about 0.05 $m^2$ to about 0.60 $m^2$. The surface area of the micro-organism filter may be about 0.185 $m^2$. The bacteria filter may also be capable of withstanding the pressure within the flow system without any appreciable change in its desired properties.

In another embodiment, the disposable housing further comprises a gas vent means in fluid communication with said flow path for removing gas from the dialysate. In one embodiment, the gas vent means comprises a sorbent gas vent downstream of the sorbent zone for removing gas from the dialysate that has been generated by contact with the sorbent zone. In a preferred embodiment, the sorbent gas vent is in fluid communication with said flow path.

In one embodiment, the gas vent means comprises a degasser, downstream of the sorbent zone, for removing gas from the dialysate. In a preferred embodiment, the degasser is in fluid communication with said flow path.

In one embodiment, the sorbent gas vent is a hydrophobic membrane. The hydrophobic membrane may be selected from polytetrafluoroethylene (Teflon®), polypropylene or other hydrophobic polymeric materials. In a preferred embodiment, gas is vented by the hydrophobic membrane by applying a positive internal pressure in the flow path or alternatively by establishing a negative pressure on the external side of the membrane. In one embodiment, positive internal pressure for degassing is provided by a suitable flow resistor, for example an orifice or filter membrane or a backpressure regulator, for example a check valve having a preselected crack pressure.

In another embodiment, the degasser comprises a vacuum degasser comprising a vacuum pump to create a negative external pressure on the external side of the hydrophobic membrane. In one embodiment, the vacuum pump is disposed in the controller. In a preferred embodiment, the interface comprises a vacuum pump connector to fluidly couple the vacuum pump of the controller with the external side of the hydrophobic membrane when said controller is connected to the disposable housing by the interface.

In a preferred embodiment, the degasser comprises a vacuum degasser comprising a pump, for example a diaphragm pump, to create a negative external pressure on the hydrophobic membrane. In a preferred embodiment, the negative pressure is controlled by a pressure sensor. The pump and pressure sensor may be disposed within the controller.

Advantageously, when the sorbent gas vent is disposed downstream of the sorbent zone, the large amount of gases that are released from the sorbent zone when the dialysate reacts with sorbent contained therein, can be quickly and effectively released from the dialysis device. More advantageously, this prevents the build up of pent up gases which may undesirably increase the pressure within the flow system. More advantageously, this also prevents dialysate from returning to a patient that contains gases which can impede dialysis treatment and may be harmful to the patient. The sorbent gas vent may be disposed within said disposable housing and is in fluid communication with the flow path therein. In one embodiment, the sorbent gas vent is disposed immediately adjacent to the sorbent zone, along said flow path for removing gas from the dialysate.

In one embodiment, the controller further comprises a control means for controlling said actuation means. Preferably, the control means is electrically coupled to a power source located in said controller. In a preferred embodiment, the control means is a pressure sensor.

In a preferred embodiment, the pressure sensor senses pressure of the dialysate flow into the flow path and the pressure of the dialysate flow in the flow path before entering the sorbent zone. The pressure sensor may also provide feedback input to a pressure regulator to regulate the pressure of the dialysate flowing to and from the dialysis device.

The pressure sensor may also provide feedback to trigger an alarm in case the detected pressure is outside an acceptable range.

In one embodiment, the disposable housing further comprises an additive dispensing means ("enrichment module") for dispensing an "additive solution" or "enrichment solution" into the dialysate.

The additive solution or enrichment solution may comprise essential substances for normal functioning of the human body, selected from the group consisting of potassium, calcium and magnesium. The substances may also include osmotic agents essential for the efficacy of dialysis, such as glucose, oligosaccharides or amino acids. In one embodiment, the additive solution comprises substances such as supplements, nutrients, vitamins and co-factors that generally promote human health. The additive solution may also include therapeutic substances such as medications and hormones.

In one embodiment, the dispenser comprises a diaphragm integrally formed with a wall of said dispenser. In one embodiment, the diaphragm is in fluid contact on one side with the additive or enrichment solution and, on another opposite side, in contact with a pressure chamber that is capable of receiving fluid therein. Pressure changes within the pressure chamber deform said diaphragm which thereby dispenses additive solution into the dialysate. In another embodiment, the dispenser may be actuated by a syringe pump. In one embodiment, the syringe pump is disposed in the controller.

In one embodiment, the additive dispensing means may be discrete from the disposable housing. This is advantageous as the enrichment module and its contents can be subjected to different sterilization techniques. For example, when the additive dispensing means contains an additive solution containing glucose heat treatment is the preferred sterilisation method. However, gamma radiation is the preferred sterilization technique for the disposable housing.

In one embodiment, the additive dispensing means comprises an interface means, such as a coupling. In one embodiment, the interface means comprises a connector that fluidly couples the additive dispensing means to the flow path disposed in the disposable housing. In one embodiment, the connector comprises a first mating part disposed on the additive dispensing means and a second mating part disposed on the disposable housing, and wherein the first and second mating parts are configured to lockingly engage with each other. In one embodiment, the first mating part disposed on the additive dispensing means and/or second mating part disposed on the disposable housing may be sealed to maintain the sterility of the additive solution in the additive dispensing means. In one embodiment, the first mating part disposed on the additive dispensing means and/or second mating part disposed on the disposable housing are sealed by means of a plug or frangible seal.

In one embodiment, the first mating part disposed on the additive dispensing means mates with the second mating part disposed on the disposable housing by breaking or puncturing or dislodging the plug or seal of the mating part. This is advantageous as it precludes the inadvertent reuse of a spent additive dispensing means in a new disposable housing.

In one embodiment, the additive dispensing means comprises a container for holding the additive solution. In one embodiment, the container may be a bag located in a rigid housing. In one embodiment, the additive dispensing means is a rigid container comprising a sponge located at an end of the container in communication with a connector. In this embodiment, the sponge facilitates delivery of the additive solution from the additive dispensing means to the dialysate flow path. In another embodiment, the container may be resiliently deformable. In one embodiment, the container is manufactured from a biocompatible plastics material. Advantageously, all these embodiments allow air-free withdrawal of the enrichment solution in the container thus enabling orientation independent use of the dialysis device.

In one embodiment, the dialysis device has an automatic dispensing system comprising a fixed displacement pump to dispense a fixed volume of additive solution to the dialysate flow path. The fixed displacement pump comprises a rigid casing defining a hollow interior. The volume of the interior may be selected from the group consisting of about 0.1 to about 10 ml; about 0.1 to about 9 ml about 0.1 to about 8 ml about 0.1 to about 7 ml about 0.1 to about 6 ml about 0.1 to about 5 ml about 0.1 to about 4 ml about 0.1 to about 3 ml about 0.1 to about 2 ml about 0.1 to about 1 ml and about 0.1 to about 0.5 ml.

In one embodiment, the fixed displacement pump comprises two chambers separated by a deformable impermeable membrane or diaphragm. In one embodiment, one of the chambers (chamber 1) is located in fluid communication with a pump, for example an air pump. The other chamber (chamber 2) is in fluid communication with the enrichment module. In one embodiment, the air pump actuates the deformable diaphragm to induce negative pressure in chamber 2 and thereby withdraws additive solution from the enrichment module. In one embodiment, the negative pressure is selected from about 30, about 40, about 50, about 60 and about 70 mmHg. In another embodiment, the air pump actuates the deformable diaphragm to apply positive pressure in chamber 2 to dispense additive solution into the dialysate in the dialysate flow path. This is advantageous as it permits a predetermined amount of additive solution to be dispensed into the dialysate flow path consistently. The volume dispensed is entirely dependent on the pump volume and is independent of dialysate pressure or flow rate.

In one embodiment, the air pump is used to actuate the storage chamber comprising a deformable diaphragm to move dialysate along the flow path, the additive dispensing means and the gas vent means. As only one pump is required for the operation of the device, the device is very energy efficient. As such the device may be powered by a battery. In one embodiment, the device comprises a rechargeable battery, such as a rechargeable lithium polymer battery.

It is a further advantage that the same controller may be used for an entire range of dialysis devices such as wearable devices, portable devices and desktop devices. Advantageously, a patient can use a wearable device for mobility during the day and a heavy duty device during sleep at home, with the same controller.

Rechargeable batteries are advantageous as the device does not have to be connected to an AC power source. As such, there is no danger of inadvertent interruption of the power supply.

In one embodiment, the rechargeable battery can be detached from the device and recharged on a separate charging unit. In another embodiment, the rechargeable battery can be recharged in situ in the dialysis device.

It is a further advantage then when the device is powered using rechargeable batteries, a patient can be moved easily while continuing the dialysis procedure, for example during an emergency or in a natural disaster scenario where no power (and water) may be available.

A battery in accordance with the disclosure may have the following exemplary characteristics:
Charging:
Maximum Charge Current: about 1200 mA
Charge Limited Voltage: about 12.6V
End-of Current: about 24 mA
Discharging:
Maximum Discharge Current: about 2400 mA
End Voltage: about 8.25V
Operation:
Temperature Charge: about 0-45
Temperature Discharge: about −20~+60

The battery may have a lifetime of greater than 100 cycles; preferably greater than 200 cycles and more preferably greater than 300 cycles of recharging.

In one embodiment, that dialysis device is only activated when the controller and disposable housing are coupled together. In one embodiment, the disposable housing is provided with a pin adapted to activate a switch located on the controller. In one embodiment, the switch may be a limit switch. When the controller and disposable housing are coupled together the pin on the disposable housing actuates the switch in the controller to connect the battery to the controller power lines. In one embodiment, the pin is deformable or breakable. This is advantageous as the broken or deformed pin cannot actuate the switch once the controller is removed from the disposable housing, thus preventing the inadvertent or intentional re-use of a used disposable unit.

In one embodiment, the disposable housing further comprises an ammonia sensor configured to detect ammonia present in said dialysate. Advantageously, the sensor for detecting ammonia present in the dialysate maximizes the utilization of the sorbent before the sorbent has to be replaced. Due to the presence of the sensor, the patient will be able to accurately identify when the sorbent of the flow system has to be replaced.

In one embodiment, the ammonia sensor is capable of detecting the concentration of ammonia present in the dialysate in the form of free ammonia or ammonium ions. The ammonia sensor may also provide a feedback input to the control system of the dialysis device so that if the ammonia concentration exceeds an undesired upper limit range, the control system may activate an alarm and/or deactivate the pump.

In one embodiment, the ammonia sensor is positioned in any part of the dialysate flow path downstream of the sorbent. In another embodiment, the ammonia sensor is located in the vacuum degasser. In particular, the ammonia sensor may be located upstream of the vacuum pump as described herein to detect ammonia in the gas emitted from the hydrophobic membrane. Alternatively, the ammonia sensor may be located to detect ammonia in an exhaust of the vacuum pump. In this embodiment, the ammonia sensor is disposed in the controller.

In one embodiment, the ammonia sensor may comprise a material or indicator strips, which change colour on exposure to or in the presence of ammonia or ammonium ions. In one embodiment, the ammonia sensor is an optochemical sensor. In another embodiment, the ammonia sensor comprises an ammonia-sensitive membrane. In another embodiment, the ammonia sensor may comprise a conductivity sensor to monitor for ammonia. In one embodiment, the ammonia sensor is an ammonia-selective potentiometric or amperometric electrode. In one embodiment, the ammonia sensor is configured to detect ammonia in gas extracted from a dialysate flow by a degasser.

In one embodiment, the ammonia sensor is disposed in the controller.

In one embodiment, the device comprises a gas vent means comprising a degasser, downstream of the sorbent zone, for removing gas from the dialysate. In one embodiment, the gas vent means is a hydrophobic membrane. In a preferred embodiment, the gas vent means comprises two hydrophobic membranes arranged in parallel. Each hydrophobic membrane is located adjacent to an air vent. In one embodiment, a hydrophilic membrane is located between the hydrophobic membranes. In one embodiment, the hydrophilic membrane is curved to facilitate the flow of gas in the dialysate to the hydrophobic membranes.

In another embodiment, the degasser is in fluid communication with an air pump to create a negative external pressure on the external side of the hydrophobic membrane. In one embodiment, the air pump is disposed in the controller. In a preferred embodiment, the interface comprises an air pump connector to fluidly couple the air pump of the controller with the external side of the hydrophobic membrane when said controller is connected to the disposable housing by the interface.

In a preferred embodiment, the degasser comprises a pump, for example an air pump, to create a negative external pressure on the hydrophobic membrane. In a preferred embodiment, the negative pressure is controlled by a pressure sensor. The pump and pressure sensor may be disposed within controller.

In one embodiment, the air vent is in fluid communication at one end with a pump, for example an air pump, located in the controller and at another end with an ammonia sensor and exhaust. In one embodiment gas is vented by the hydrophobic membrane by applying a positive internal pressure in the dialysate flow path or alternatively by establishing a negative pressure on the external side of the membrane. In one embodiment, positive internal pressure for degassing is provided by a suitable flow resistor, for example an orifice or filter membrane or a backpressure regulator, for example a check valve having a preselected crack pressure. In one embodiment, the disposable housing comprises an outflow conduit for transmission of dialysate from said patient's body and an inflow conduit for transmission of dialysate to said patient's body.

In one embodiment, the degasser is disposed in the disposable housing.

In one embodiment, the disposable housing may be disposed of on a daily basis or after each dialysis cycle. It is an advantage of the device that as the flow path is fluidly sealed from the controller the sterility of the device can be maintained, or at least ameliorated, by daily disposal of the disposable housing. It is a further advantage of the device that as only one connection is required between the disposable housing and the patient, the risk of biological contamination of the device is significantly reduced. It is a further advantage that the connector between the disposable housing and the controller is fluidly sealed to prevent biological or chemical contamination of the device. It is an advantage of the device that, as the flow path is fluidly sealed from the controller, the risk of biological and/or chemical contamination of the dialysate by the controller is significantly reduced.

In one embodiment, the flow path through which the dialysate flows may be made of resilient, chemically and biologically inert materials. In one embodiment, the flow path may also be able to withstand the pressure within the dialysis device without leakage. In one embodiment, the flow path is manufactured from medical grade polymer such as polycarbonate, nylon, silicone or polyurethane. Other components of the flow system may also be connected using a connector made of resilient material such as of medical grade polymer as nylon or polycarbonate or polysulphone.

In one embodiment, the flow system further comprises a conductivity sensor. In another embodiment, the flow system further comprises a urea sensor. In another embodiment, the flow system further comprises a creatinine sensor. In a further embodiment, the flow system comprises a glucose sensor. In one embodiment, these further sensors may be located downstream of the sorbent in the flow path. In one embodiment, these sensors may be disposed along the dialysate flow path adjacent to or within the degasser.

It is an advantage of the device of the disclosure that due to the requirement for only one pump and a deformable diaphragm integrally formed with a wall of the storage chamber that the overall size of the device can be significantly reduced relative to other dialysis devices.

In one embodiment, the disposable housing may be provided with a tamper proof seal. In another embodiment, the controller may be provided with a tamper proof seal. The tamper proof seal may be located on the conduit connector disposed on the controller or disposable housing. This is advantageous, as the tamper proof seal will ensure that the controller or disposable housing are sterile before use. The tamper proof seal will also prevent a controller of disposable housing that has been tampered with from being used in a dialysis cycle. This is further advantageous as biological or chemical contamination of the device, and the risk of patient infection is further reduced.

There is also provided a dialysis controller operable with a disposable housing having fluid displacement means configured to move dialysate along a flow path disposed within said housing, the controller comprising actuation means for actuating said fluid displacement means and an interface for connecting said controller to said disposable housing, wherein said controller and said interface are fluidly sealed from said flow path during operation of the disposable housing.

There is also provided a disposable dialysis housing that is configured to be operated by a controller, the disposable housing comprising:

a flow path disposed therein along which dialysate received from a patient is subjected to contaminant removal when in operation; and an interface for connecting said housing to a corresponding interface of said controller, wherein in use, said flow path is fluidly sealed from said controller and said interface.

There is also provided a dialysis system comprising:

a disposable housing having a flow path containing dialysate received from a patient, the dialysate undergoing contaminant removal while disposed in the flow path;

a controller operably connected to said disposable housing by an interface to control the operations of the disposable housing;

wherein said flow path is fluidly sealed from the controller and interface.

In one embodiment, the system comprises a pressure sensor configured to determine fluid pressure changes in the flow path. In another embodiment, the controller is configured to determine the flow rate of dialysate in the flow path based on the pressure changes output by the pressure sensor.

In one embodiment, the controller comprises a computer program encoded in at least one computer readable medium, the computer program comprising a set of instructions, encoded in at least one computer readable medium, operable to implement, when executed by a processor, calculating the flow rate of dialysate in the flow path based on said pressure changes output by said pressure sensor.

In one embodiment, the controller comprises a computer program encoded in at least one computer readable medium, the computer program comprising a set of instructions, encoded in at least one computer readable medium, operable to implement, when executed by a processor, calculating the use time of the sorbent cartridge based on the start time of dialysis using a new disposable housing comprising a sorbent zone. In one embodiment, the start time is correlated with a predetermined lifetime of the sorbent zone in the disposable housing. In one embodiment, the use time of the sorbent zone is monitored in real time. In one embodiment, when the processor detects that the use time is equal to the predetermined lifetime of the sorbent zone, dialysis is stopped. This is advantageous, as dialysis will be stopped thus preventing overuse of the sorbent zone and reducing any untreated dialysate being sent back to the patient.

There is also provided a dialysis method implemented in a dialysis system comprising a disposable housing having a flow path extending therethrough and a sorbent zone for contaminant removal, an interface operably coupling said disposable housing to a controller for controlling the passage of dialysate along the flow path of said disposable housing, the method comprising the steps of:

passing a dialysate along the flow path of said disposable housing while ensuring that the flow path and dialysate therein is fluidly sealed from the interface and the controller.

In one embodiment, the method comprises the step of:

measuring pressure changes in the dialysate flow path during said passing step; and determining the flow rate of dialysate along said dialysate flow path according to changes in said measured pressure.

In one embodiment, the method further comprises the step of adjusting the determined flow rate to a target flow rate.

There is also provided a dialysis system comprising:

a disposable housing having a flow path containing dialysate received from a patient, the dialysate undergoing contaminant removal while disposed in the flow path;

a pressure sensor configured to determine fluid pressure changes in the flow path.

a controller operably connected to said disposable housing by an interface to control the operations of the disposable housing and wherein the controller is configured to determine the flow rate of dialysate in the flow path based on the pressure changes output by the pressure sensor.

In one embodiment, the controller comprises a computer program encoded in at least one computer readable medium, the computer program comprising a set of instructions, encoded in at least one computer readable medium, operable to implement, when executed by a processor, a calculation of the flow rate of dialysate in the flow path based on the pressure changes output by the pressure sensor.

In one embodiment, said determining step comprises the steps of:

a). applying a first preselected pressure to a flow path to permit a volume of dialysate to enter or exit said flow path;

b). detecting a second preselected pressure in said storage chamber as a result of the entry or exit of dialysate to or from said flow path;

c). determining the volume of dialysate that has entered or exited the flow path, and d). correlating the time required to reach said second preselected pressure with the volume of dialysate that has entered or exited said flow path to determine the flow rate of the dialysate in the dialysis device.

In one embodiment, the controller comprises a further computer program encoded in at least one computer readable medium, the further computer program comprising a set of instructions, encoded in at least one computer readable medium, operable to implement, when executed by a processor, an iterative optimisation of said preselected pressure based on said determined flow rate of dialysate in the flow path.

There is also provided the use of a dialysis device according the disclosure, to treat a patient suffering from kidney malfunction.

There is also provided a kit comprising the dialysis device according to the disclosure, together with instructions for use.

There is also provided a kit comprising the controller according to the disclosure, together with instructions for use.

There is also provided a kit comprising the disposable housing according to the disclosure, together with instructions for use.

BRIEF DESCRIPTION OF DRAWINGS

The accompanying drawings illustrate a disclosed embodiment and serve to explain the principles of the disclosed embodiment. It is to be understood, however, that the drawings are designed for purposes of illustration only, and not as a definition of the limits of the invention.

FIG. 1F is a schematic diagram of one embodiment of the disclosed dialysis device.

FIG. 2A is a schematic diagram of an alternative embodiment of the disclosed dialysis device, wherein the flow of the dialysate is toward the storage chamber from the peritoneal cavity.

FIGS. 9A and 9B are cross sectional views of a sealed connector of the additive dispensing means in accordance with the disclosure.

FIGS. 10A and 10B are cross sectional views of an embodiment of an additive dispensing means in accordance with the disclosure.

FIGS. 12A-C are cross sectional views of an embodiment of an automatic dispensing system in accordance with the disclosure.

In the figures, like numerals denote like parts.

DETAILED DESCRIPTION OF DRAWINGS

Figure 1A:
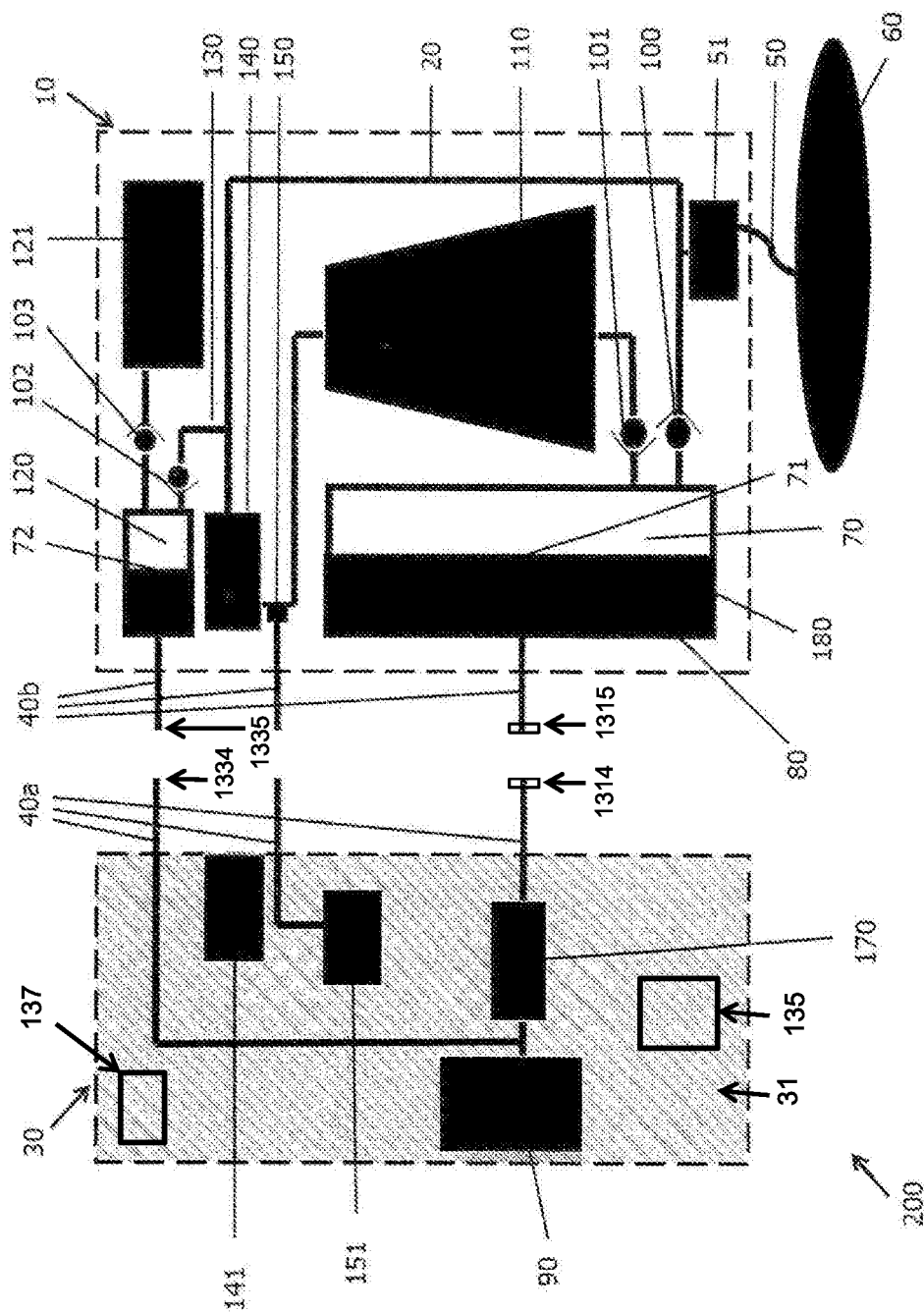
FIG. 1A is a schematic diagram of one embodiment of the disclosed dialysis device.

Referring to FIG. 1A, there is shown one embodiment of the disclosed dialysis device (200).

The dialysis device comprises a disposable housing (10) having a flow path in the form of conduit (20), a controller (31) in the form of a control housing (30) for controlling the operation of the disposable housing (10). The dialysis device is powered by a battery (137). In this figure the disposable housing (10) and control housing (30) are not operably connected to each other. The disposable housing (10) and control housing (30) comprise interface in the form of a conduit connector (40a) disposed on said control housing (30) and (40b) disposed on the disposable housing (10) capable of connecting the control housing and the disposable housing. The disposable housing (10) and control housing (30) are brought into operative engagement when the conduit connector (40a) is brought into locking engagement with conduit connector (40b) The conduit (20) of the disposable housing (10) is fluidly sealed from the control housing (30) and conduit connector (40a,40b).

The dialysis device comprises a flexible dialysate tube (50) which is capable of being in fluid communication with the peritoneal cavity (60) and a conduit (20). The dialysis device further comprises a storage chamber (70) located in a rigid compartment (180). The storage chamber (70) comprises a deformable diaphragm (71) integrally formed in one of the walls of the storage chamber (70). The deformable diaphragm (71) is in fluid communication on one side with the dialysate conduit (20) and, on another opposite side, in fluid communication with a pressure chamber (80). When the disposable housing (10) and control housing (30) are operably coupled to each other, the conduit connector (40a, 40b) fluidly couples the pressure chamber (80) of the disposable housing (10) to a pump (90) located in the control housing (30). The conduit connector (40a,40b) comprises a first mating part (1314) and a second mating part (1315).

The pump (90) is configured to actuate the deformable diaphragm (71), by inducing a pressure change in the pressure chamber (80) which deforms the deformable diaphragm (71) and thereby moves dialysate within said dialysate conduit (20). The controller (31) comprises a computer (135) configured to act on instructions for operation of the pump (90).

Check valves (100,101,102,103) are disposed along the conduit (20) and are configured to, in the outflow mode, allow the dialysate to flow from the peritoneal cavity (60) to the storage chamber (70), and in the inflow mode allow the dialysate to flow from the storage chamber (70) to said sorbent zone (110) for removal of contaminants therein, and further permit the dialysate substantially free of said contaminants to flow back to the peritoneal cavity (60).

The disposable housing is also provided with an enrichment module (120), for dispensing a preselected amount of an enrichment solution into the dialysate, in fluid communication with the conduit (20) via a conduit (130). The enrichment module is also in fluid communication with an enrichment solution reservoir (121). The pump (90) is in fluid communication with a deformable membrane (72) of the enrichment module 120 via conduit connector (40a,40b), when the disposable housing (10) and control housing (30) are in operable engagement. The conduit connector (40a, 40b) comprises a first mating part (1334) and a second mating part (1335).

An ammonia sensor (140) is also provided downstream of the sorbent zone (110) to detect any ammonia in the dialysate. Ammonia is detected by the ammonia detector (141) when the disposable housing (10) and control housing (30) are operably coupled to each other.

A degasser in the form of a hydrophobic membrane (150) is also located downstream of the sorbent zone. The external side of the hydrophobic membrane (150) is in fluid communication with a vacuum pump (151) via the conduit connector (40a,40b) when the control housing and disposable housing are operably coupled.

Figure 1B:
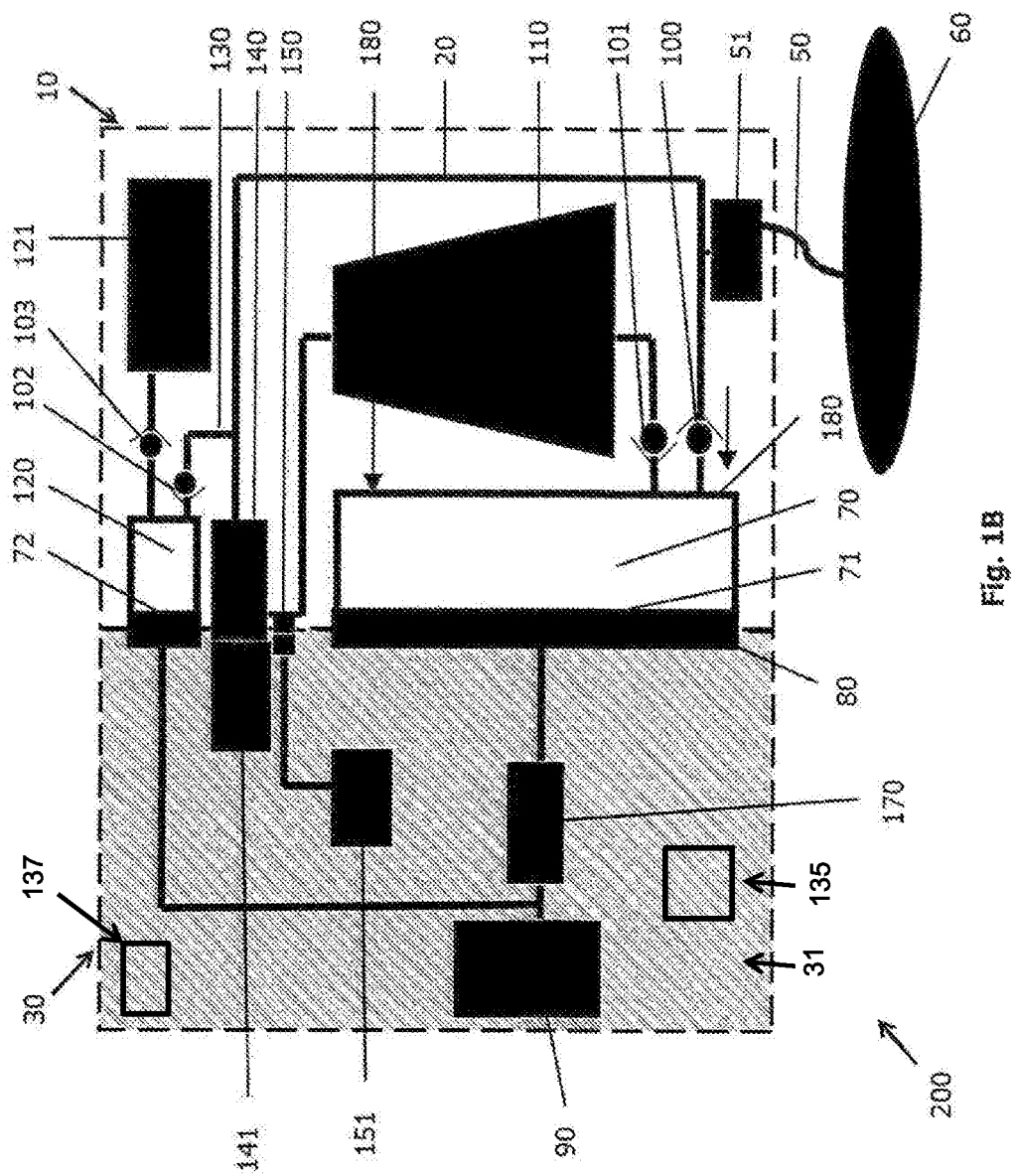
FIG. 1B is a schematic diagram of one embodiment of the disclosed dialysis device, wherein the flow of the dialysate is toward the storage chamber from the peritoneal cavity.

Referring now to FIG. 1B, there is the embodiment of FIG. 1A showing the disposable housing (10) and control housing (30) operably coupled with each other, operating in an outflow mode, wherein the flow of the dialysate is toward the storage chamber (70) from the peritoneal cavity (60) of a patient. The pump (90) actuates the deformable diaphragm (71), by inducing negative pressure in the pressure chamber (80). The negative pressure in the pressure chamber (80) deforms the deformable diaphragm (71) by biasing the deformable diaphragm (71) in the direction of arrow A and thereby moves dialysate from said peritoneal cavity (60) of the patient into the dialysate conduit (20) via bubble trap (51). The dialysate flows to the storage chamber (70) through check valve (100). A pressure sensor (170) is located in operable communication with the pump (90) to establish a preselected negative pressure within the pressure chamber (80) and to determine if the pressure of the dialysate being withdrawn from the peritoneal cavity (60) is within a safe limit.

The pump (90) operates intermittently under the control of the pressure sensor (170) to maintain the negative pressure in the pressure chamber (80) within a preselected range. Once the storage chamber (70) is full of dialysate, this is detected by the pressure sensor (170), triggering the inversion of the pump direction and thus converting the system to an inflow mode.

The pump 90 is also in fluid communication with a diaphragm (72) integrally formed in a wall of said enrichment module (120). At the same time as the storage chamber (70) is actuated under negative pressure, the enrichment module (120) is also actuated under negative pressure by the pump (90), such that a predetermined amount of an enrichment solution is withdrawn from an enrichment solution reservoir (121) though check valve (103) into the enrichment module (120). Check valve (102) ensures that no dialysate is withdrawn into the enrichment module (120) from the conduit (20).

Figure 1C:
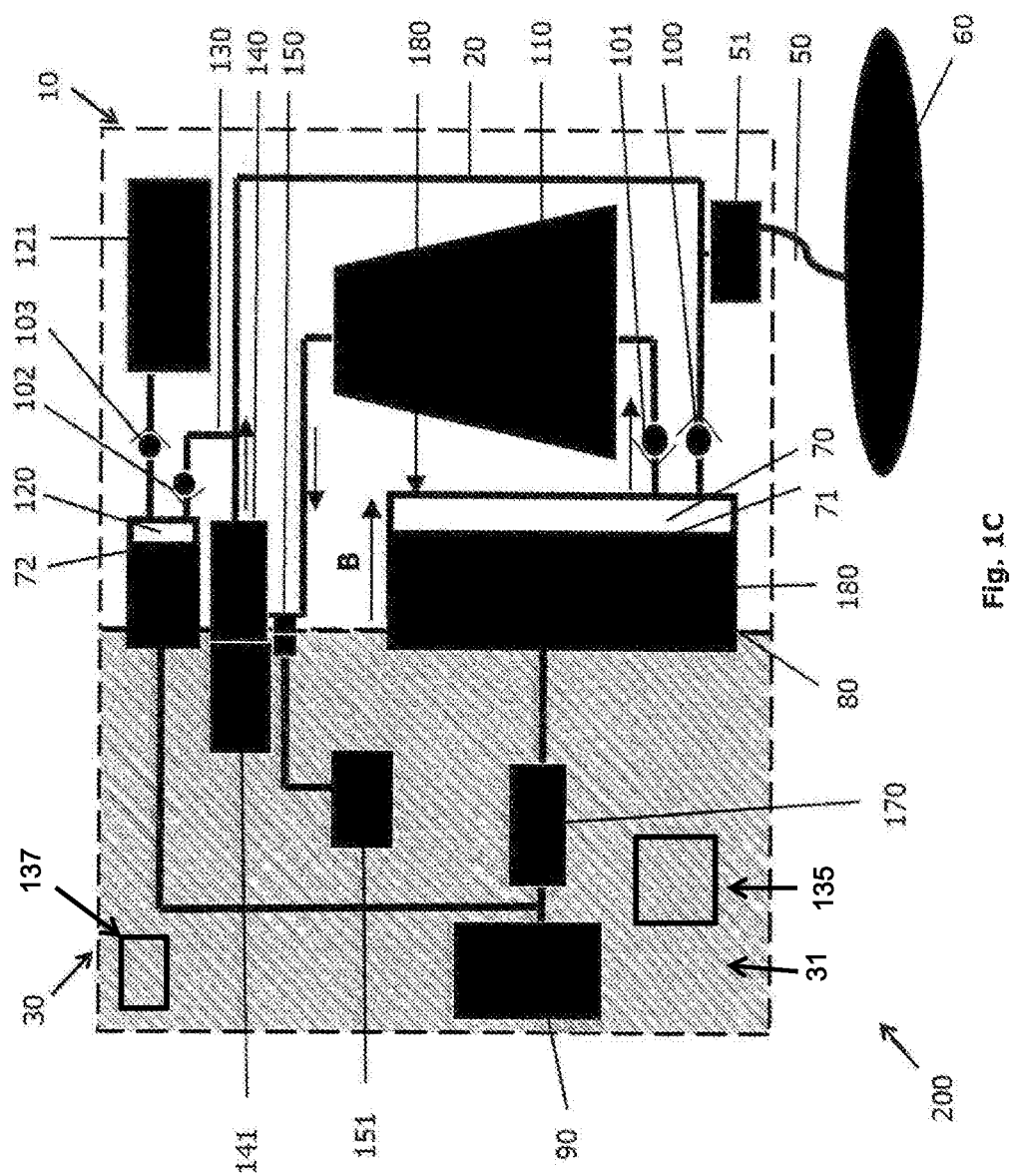
FIG. 1C is a schematic diagram of one embodiment of the disclosed dialysis device, wherein the flow of the dialysate is from the storage chamber to the peritoneal cavity.

Referring to FIG. 1C, the flow system of FIG. 1B is shown in the inflow mode, wherein the flow of the dialysate is from the storage chamber (70) to the peritoneal cavity (60). Once the storage chamber (70) is full, the pump (90) actuates the deformable diaphragm (71), by inducing positive pressure in the pressure chamber (80).

The positive pressure in the pressure chamber (80) deforms the deformable diaphragm (71) by biasing the deformable diaphragm (71) in the direction of arrow B and thereby moves dialysate from the storage chamber (70) and check valve (100) closes preventing dialysate from returning to the peritoneal cavity (60) before being treated to remove contaminants.

The pressure sensor (170) monitors the pressure in the pressure chamber (80) to ensure that the pressure of the dialysate being returned to the peritoneal cavity (60) in the inflow mode is within a safe limit.

The dialysate flows from the storage chamber (70) into the sorbent zone (110) through check valve (101). The regenerated dialysate from the sorbent zone (110) then flows past a degasser in the form of a hydrophobic membrane (150). The external side of the membrane is subjected to negative pressure by a vacuum pump (151) to aid the removal of gas generated during the dialysis procedure. The dialysate then flows through an ammonia sensor (140) which monitors the level of ammonia in the regenerated dialysate, to ensure that the ammonia level does not exceed a safe limit, prior to returning to the peritoneal cavity (60) of a patient. Ammonia is detected by the ammonia detector (141).

The regenerated dialysate then flows past an enrichment module (120). In the inflow mode, the pump (90) actuates the diaphragm (72) of the enrichment module (120), which has previously been primed with a volume of enrichment solution from the enrichment solution reservoir (121), under positive pressure. As the enrichment module (120) is actuated, check valve (103) closes to ensure that the enrichment solution does not flow back into the enrichment solution reservoir (121). The enrichment module (120) then dispenses a preselected amount of enrichment solution containing desired substances, such as electrolytes, osmotic agents, nutrients, medication and the like, into the dialysate conduit (20) through check valve (102) and conduit (130).

The regenerated dialysate then flows back to the peritoneal cavity (60) through the bubble trap (51) and flexible dialysate conduit (50).

As in the outflow mode, the pump (90) is operated intermittently under the control of the pressure sensor (170) to maintain the positive pressure in the pressure chamber (80) within a preselected range. Once the storage chamber is empty of dialysate, the pressure sensor (170) detects this and inverts the pump direction and converts the system to the outflow mode to repeat the dialysis cycle.

Figure 1D:
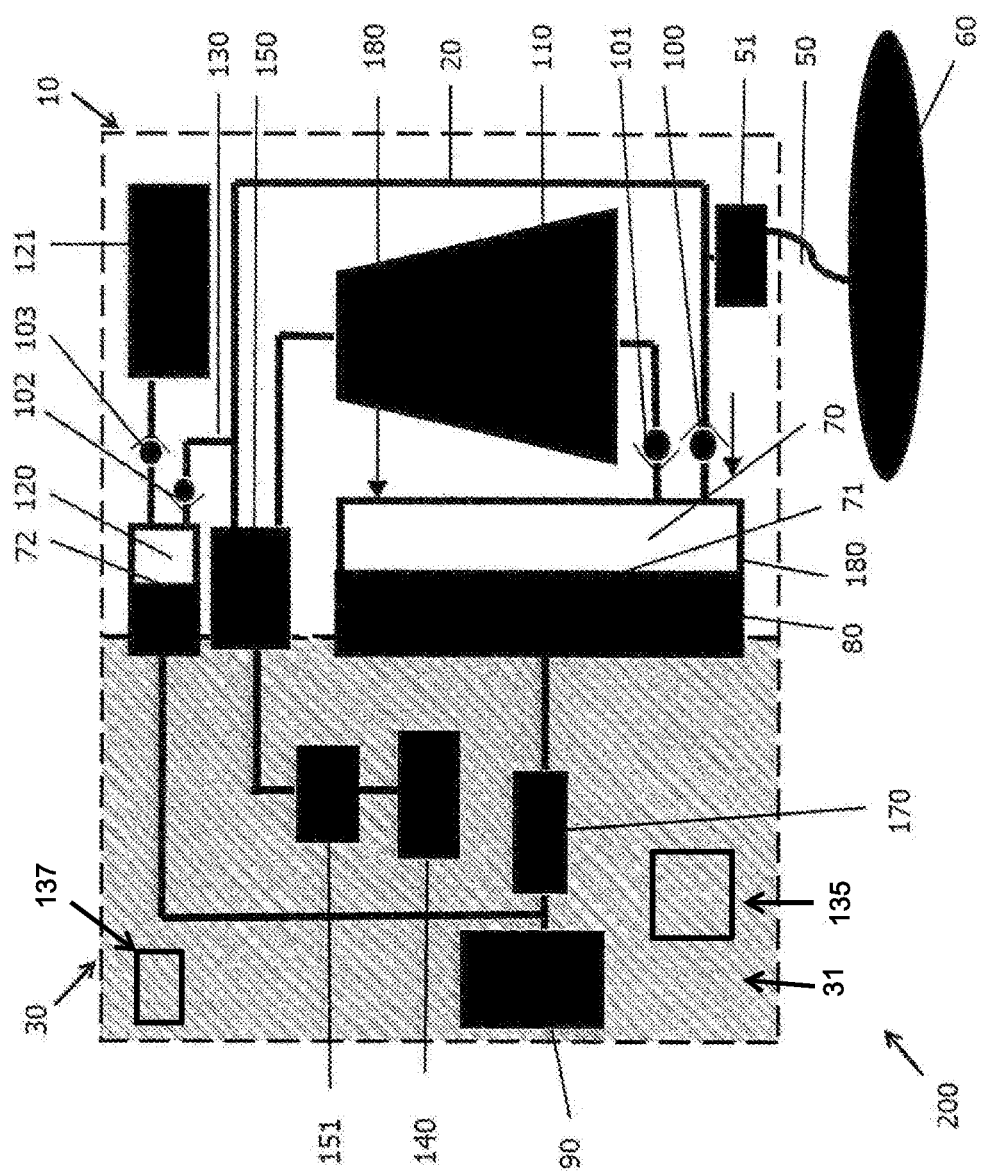
FIG. 1D is a schematic diagram of one embodiment of the disclosed dialysis device.

Referring to FIG. 1D, there is presented an alternative embodiment of the dialysis device according to the disclosure. The dialysis device (200) works in essentially the same way as the device described in FIGS. 1A-C. The regenerated dialysate from the sorbent zone (110) flows past a degasser in the form of a hydrophobic membrane (150). The external side of the membrane is subjected to negative pressure by a vacuum pump (151) in fluid communication with the hydrophobic membrane to aid the removal of gas generated during the dialysis procedure. Differing from FIGS. 1A-C, the gas vented from the dialysate is then passed through an ammonia sensor (140) located in the control housing (30). The ammonia sensor monitors the level of ammonia in the gas vented from the dialysate to ensure that the ammonia level does not exceed a safe limit, prior to returning the dialysate to the peritoneal cavity (60) of a patient.

Figure 1E:
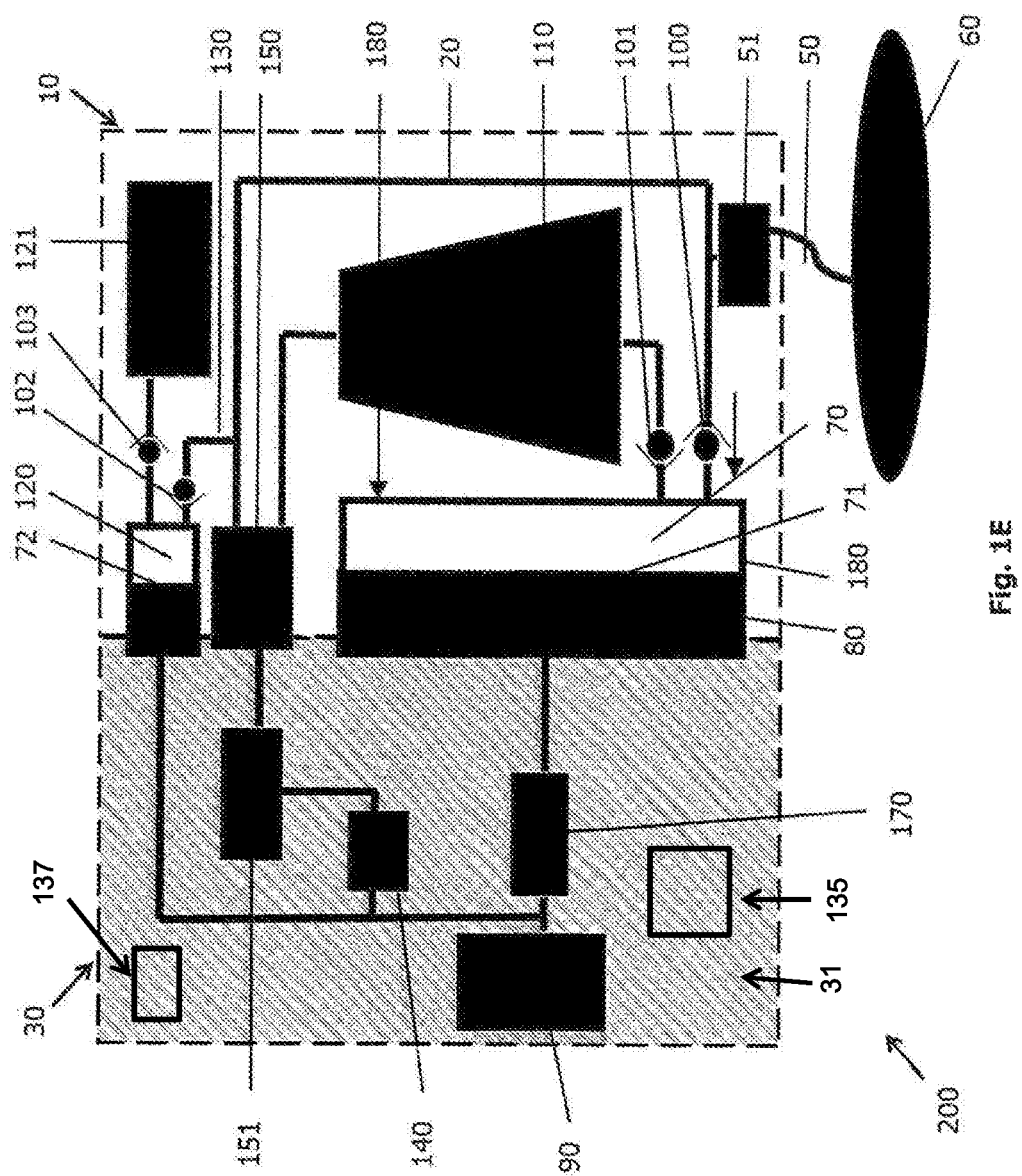
FIG. 1E is a schematic diagram of one embodiment of the disclosed dialysis device.

Referring to FIG. 1E, there is shown an alternative embodiment of the dialysis device according to the disclosure. The dialysis device (200) works in essentially the same way as the device described in FIGS. 1A-C. However, the pump (90) also subjects the hydrophobic membrane (150) via the conduit connector (not shown) and valve (104) to negative pressure during an outflow mode (where dialysate is received from a patient's peritoneal cavity (60) via a flexible dialysate tube (50)). Valve (104) ensures that no gas is introduced into the dialysate path via the hydrophobic membrane (150) during an inflow mode, when the pump (90) subjects the pressure chamber (80) to positive pressure. Ammonia gas released from the dialysate is then detected by the ammonia sensor (140).

Referring to FIG. 1F, there is shown an alternative embodiment of the dialysis device according to the disclosure. The dialysis device (200) works in essentially the same way as the device described in FIGS. 1A-C. However, the pump (90) is in fluid communication with both the pressure chamber (80) and the enrichment module (120) via a single connection (41) in the disposable housing (10). The pump (90) also subjects the degasser in the form of a hydrophobic membrane (150) to negative pressure during an outflow mode (where dialysate is received from a patient's peritoneal cavity (60) via a flexible dialysate tube (50)). During an inflow mode the pump (90) subjects the pressure chamber (80) to positive pressure. Valve (104) ensures that no gas is introduced into the dialysate path via the hydrophobic membrane (150) during an inflow mode, when the pump (90) subjects the pressure chamber (80) to positive pressure. Ammonia gas released from the dialysate is then detected by the ammonia sensor (140).

Referring to FIG. 2A, there is presented an alternative embodiment of the flow system (201) in accordance with the present disclosure wherein the flow of the dialysate is toward the storage chamber (70) from the peritoneal cavity (60), i.e. outflow mode. The pump (90) actuates the deformable diaphragm (71), by inducing negative pressure in the pressure chamber (80). The negative pressure in the pressure chamber (80) deforms the deformable diaphragm (71) by biasing the deformable diaphragm (71) in the direction of arrow A and thereby moves dialysate from said peritoneal cavity (60) of the patient into the dialysate conduit (20) via bubble trap (51). The dialysate flows to the storage chamber (70) located in a rigid compartment (180) through check valve (100). A pressure sensor (170) is located in operable communication with the pump (90) to establish a preselected negative pressure within the pressure chamber (80) and to determine if the pressure of the dialysate being withdrawn from the peritoneal cavity (60) is within a safe limit.

The pump (90) operates intermittently under the control of the pressure sensor (170) to maintain the negative pressure in the pressure chamber (80) within a preselected range. Once the storage chamber (70) is full of dialysate, this is detected by the pressure sensor (170) which inverts the pump direction and converts the system to an inflow mode.

An enrichment module (120) is provided in fluid communication with the conduit (20) via a conduit (130). The enrichment module (120) is configured to be actuated by a syringe pump (91) in the inflow mode.

Figure 2B:
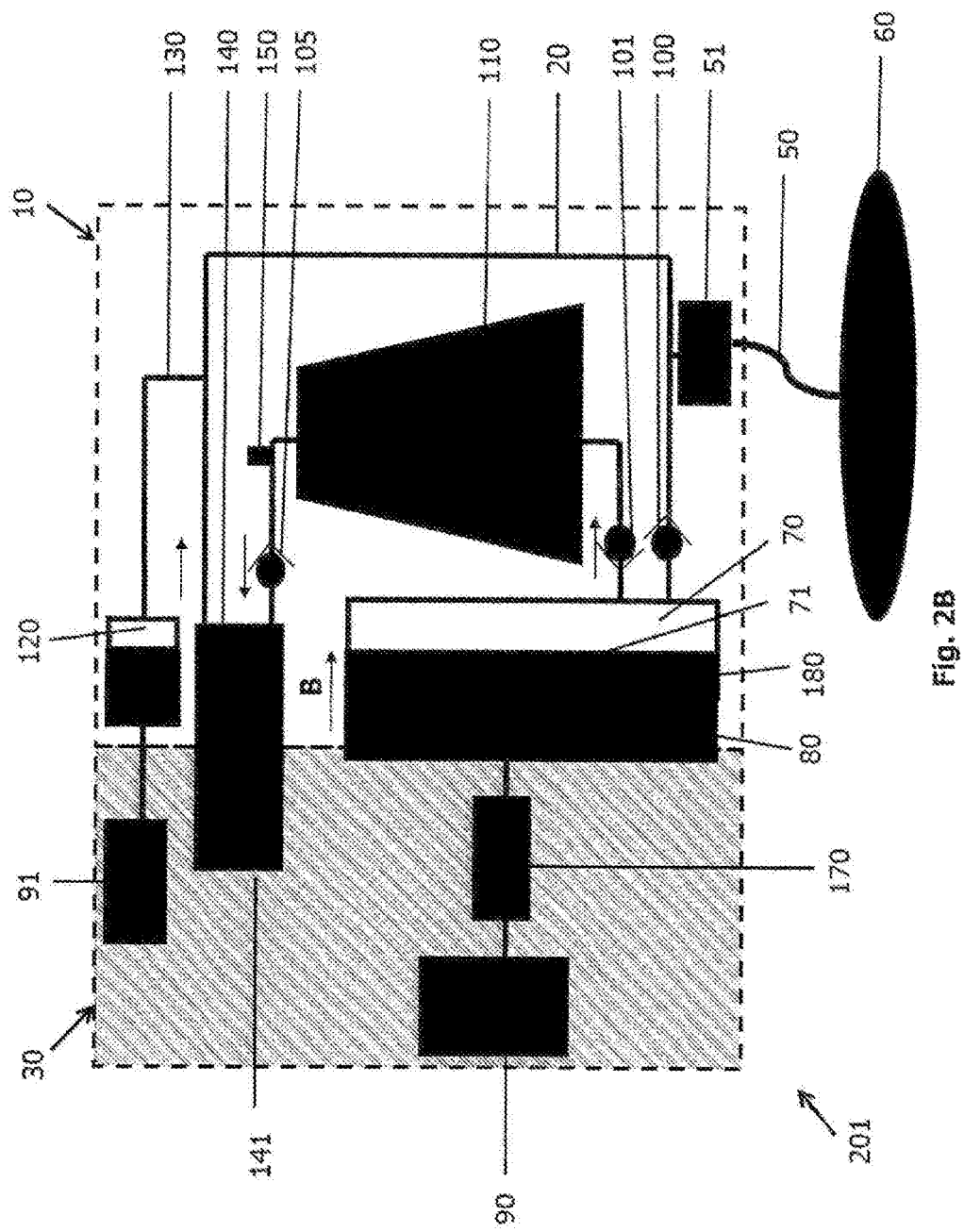
FIG. 2B is a schematic diagram of the embodiment of FIG. 2A, wherein the flow of the dialysate is from the storage chamber toward the peritoneal cavity.

Referring to FIG. 2B, the flow system of FIG. 2A is shown in the inflow mode, wherein the flow of the dialysate is from the storage chamber (70) to the peritoneal cavity (60). Once the storage chamber (70) is full, the pump (90) actuates the deformable diaphragm (71), by inducing positive pressure in the pressure chamber (80). The positive pressure in the pressure chamber (80) deforms the deformable diaphragm (71) by biasing the deformable diaphragm (71) in the direction of arrow B and thereby moves dialysate from the storage chamber (70) and check valve (100) closes preventing dialysate from returning to the peritoneal cavity (60) before being treated to remove contaminants.

The pressure sensor (170) monitors the pressure in the pressure chamber (80) to ensure that the pressure of the dialysate being returned to the peritoneal cavity (60) in the inflow mode is within a safe limit.

The dialysate flows from the storage chamber (70) into the sorbent zone (110) through check valve (101). The regenerated dialysate from the sorbent zone (110) flows past a degasser in the form of a hydrophobic membrane (150) located upstream of a check valve (105). The presence of check valve (105) results in a positive pressure gradient across the hydrophobic membrane which permits the removal of any unwanted gas emitted during the dialysis operation. The dialysate then flows through an ammonia sensor (140) which monitors the level of ammonia in the regenerated dialysate, to ensure that the ammonia level does not exceed a safe limit, prior to returning to the peritoneal cavity (60) of a patient.

The regenerated dialysate then flows past an enrichment module (120). In the inflow mode, the syringe pump (91) actuates the enrichment module (120), which contains a volume of enrichment solution under positive pressure. The enrichment module (120) then dispenses a preselected amount of enrichment solution containing desired substances, such as electrolytes, osmotic agents, nutrients, medication and the like, into the dialysate conduit (20) via conduit (130). The syringe pump (91) only operates in the inflow mode.

The regenerated dialysate then flows back to the peritoneal cavity (60) through the bubble trap (51) and flexible dialysate conduit (50).

As in the outflow mode, the pump (90) is operated intermittently under the control of the pressure sensor (170) to maintain the positive pressure in the pressure chamber (80) within a preselected range. Once the storage chamber is empty of dialysate, the pressure sensor (170) detects this and inverts the pump direction and converts the system to the outflow mode to repeat the dialysis cycle.

Figure 3:
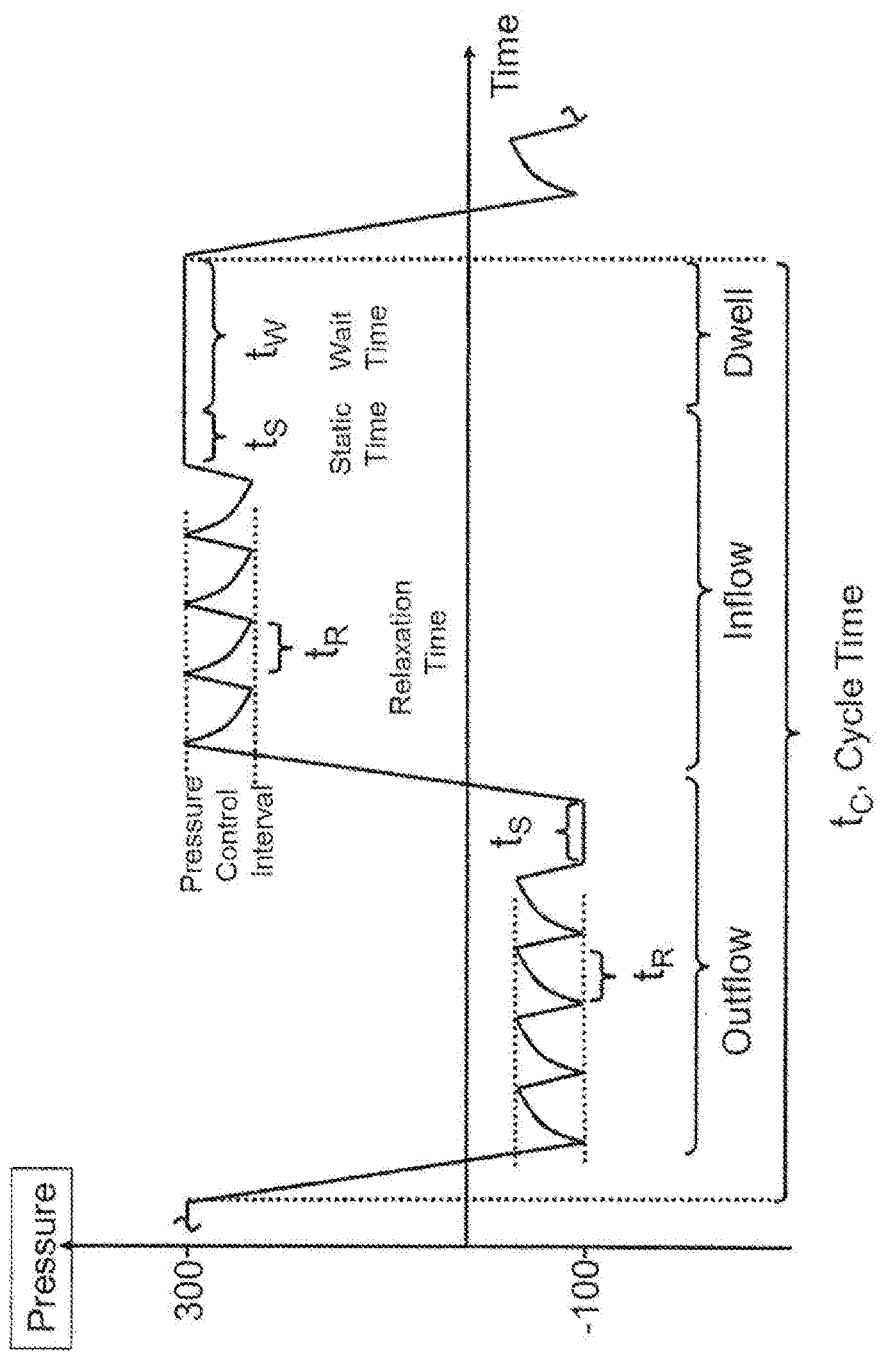
FIG. 3 is a graphic representation of the flow control of the dialysate according to an embodiment of the present disclosure.

FIG. 3, shows a graphic representation of the flow control of dialysate in an embodiment of the dialysis device according to the present disclosure. The phases of the flow control in FIG. 3 are separated into "outflow, "inflow" and "dwell".

In an outflow mode, a negative actuating pressure is produced by a pump, which is operated intermittently under the control of a pressure sensor. As can be seen in FIG. 3, the negative pressure in the pressure chamber is maintained within the limits of a preselected upper and lower pressure. Unobstructed flow of dialysate is indicated by continuous (rapid) relief of (negative) pressure during the off-times of the pump. The measurement of the time which passes during the pressure relief ($t_R$—relaxation time) may be used to estimate the effected fluid flow speed. When the storage chamber is full of dialysate, the pressure cannot be relieved anymore and the pressure becomes static for a period of time ($t_S$—static time). This is detected by a pressure sensor, which triggers the reversal of the pump to an inflow mode. The average "outflow" flow rate is equal to the volume of the storage chamber ("tidal volume") divided by the time required to fill the storage chamber completely. This rate is dependent on the choice of preselected pressure limits and can be modified accordingly.

During the inflow mode, a positive actuating pressure is produced by the pump. The dialysate contained in the storage chamber is subsequently forced through the sorbent zone of the device and is then returned to the patient. The pump is operated intermittently, such that the positive pressure is regulated between preselected upper and lower pressure limits. The fluid in the storage chamber is forced through the sorbent cartridge, thereby relieving the (positive) pressure. The duration of this relief can be used to estimate the flow rate ($t_R$—relaxation time). When the pump chamber is empty, the pressure cannot be relieved anymore and the pressure becomes static for a period of time ($t_S$—static time), indicating completion of the "inflow" phase. The average "inflow" flow rate equals the volume of the storage chamber divided by the time required to complete "inflow".

FIG. 3 also shows a wait time or "dwell" time ($t_W$). This period is used to control the overall fluid exchange rate: overall flow rate equals storage chamber volume (tidal volume) divided by the total cycle time ($t_C$=outflow+inflow+dwell). For example, if a specific overall exchange rate is desired, then the system can use the dwell time as a flexible wait time until the desired total cycle time has passed.

Figure 4A:
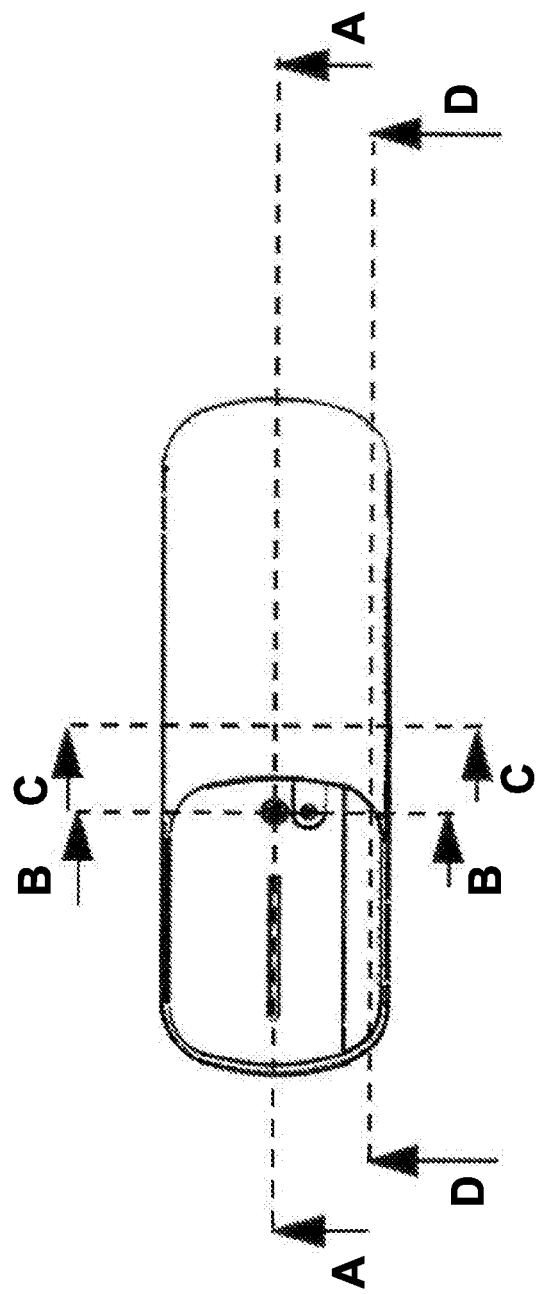
FIGS. 4A-D are cross sectional views of a prototype of a disposable housing in accordance with an embodiment of the present disclosure.
Figure 4B:
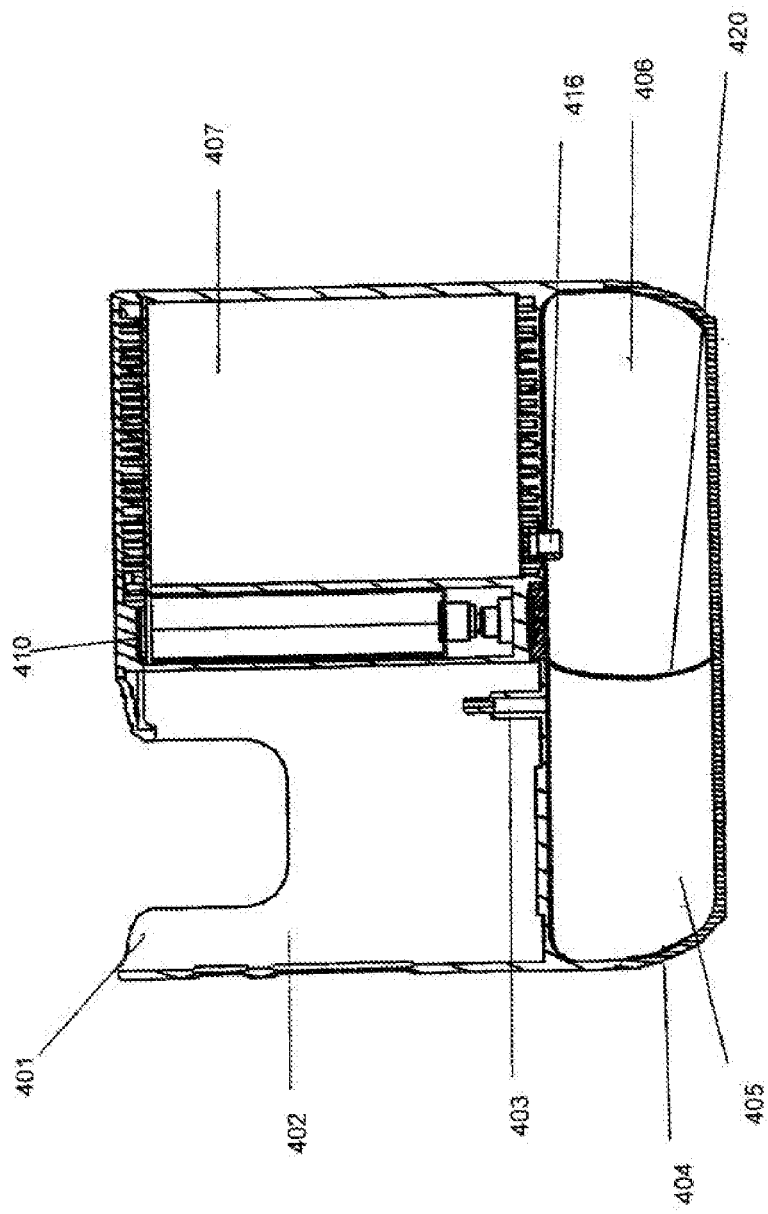

FIG. 4A shows a prototype disposable housing (400) in accordance with an embodiment of the present disclosure. FIG. 4B shows a cross sectional view of the disposable housing taken along axis A-A of FIG. 4A. The disposable housing comprises an enclosure (401) defining an interior (402) for receiving a control housing (not shown) via a conduit connector (403). The disposable housing comprises a rigid compartment (404) defining a pressure chamber (405) in which a storage chamber (406) is disposed. The storage chamber has a deformable diaphragm (420) integrally formed in a wall thereof. The storage chamber (406) is in fluid communication with a sorbent zone (407), via a fluid channel (416).

The sorbent zone (407) comprises a check valve (409, see FIGS. 4C and 4D) in fluid communication with a degasser in the form of a hydrophobic membrane (410).

Figure 4C:
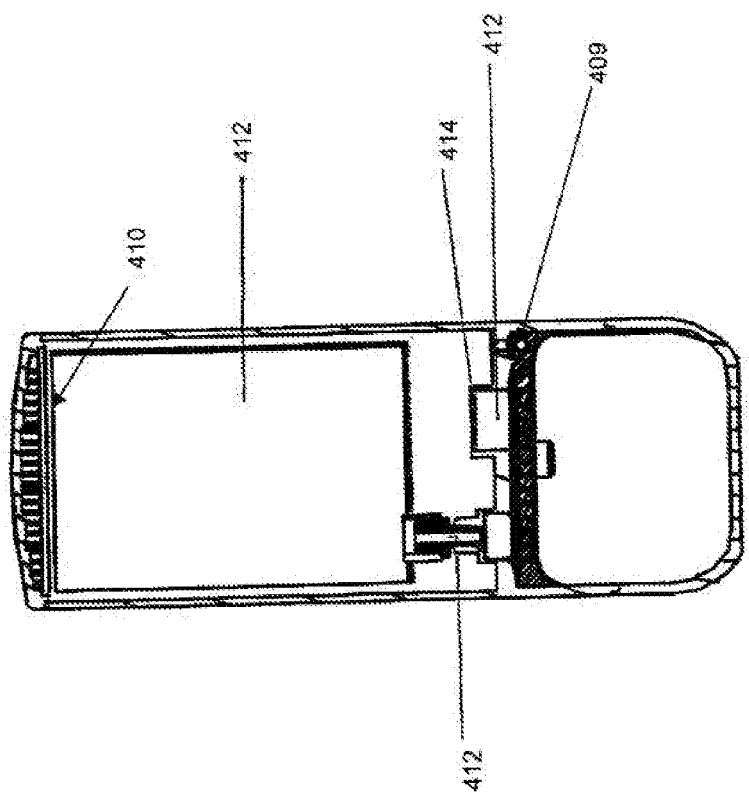

FIG. 4C provides a cross-sectional view of the sorbent module along axis C-C of FIG. 4A. An enrichment module (411) is in fluid communication with an enrichment solution reservoir (412) via a check valve (413). The enrichment module (411) is also in fluid communication with the conduit of dialysate via check valve (414).

Figure 4D:
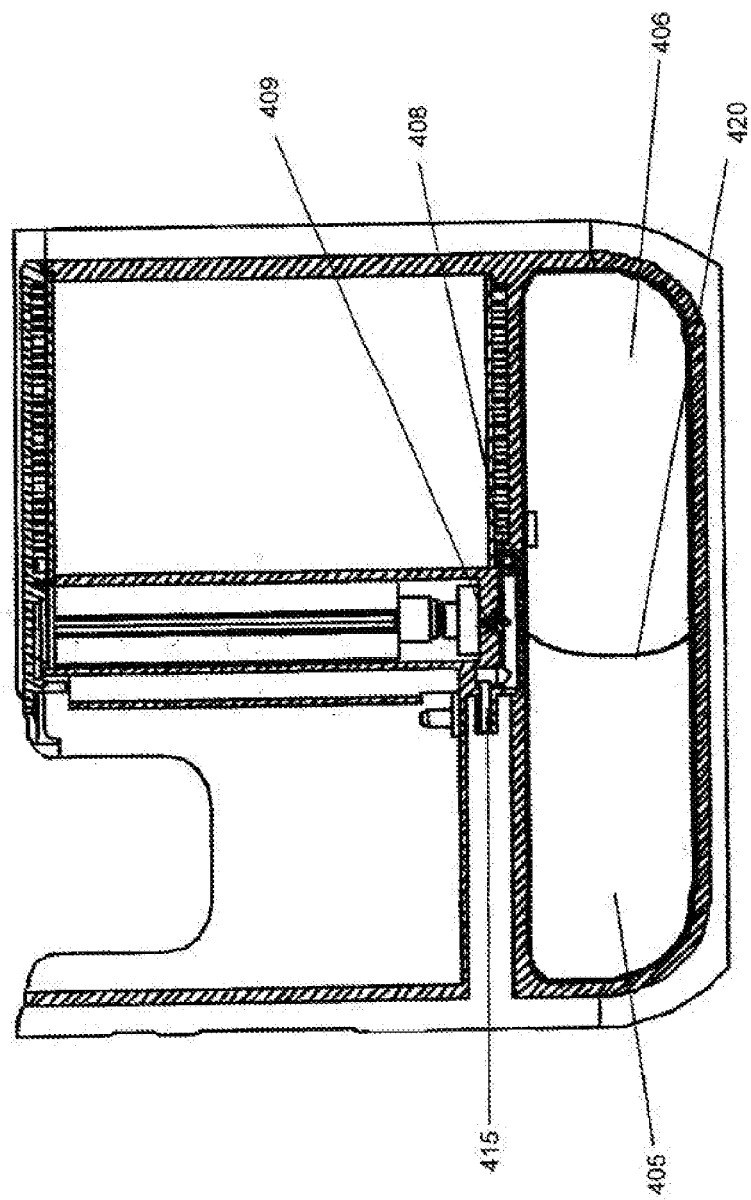

FIG. 4D provides a cross-sectional view of the sorbent module along axis D-D of FIG. 4A. The regenerated dialysate exits the disposable housing via check valve (409) and outlet (415).

In use during an outflow mode, the control housing (not shown) is located in the interior (402) of the disposable housing (400, see FIGS. 4A and 4B). The pump in the control housing actuates the deformable diaphragm (420) located in the wall of the storage chamber (406), via the conduit connector (403, see FIG. 4B) by transmitting pump fluid from the conduit connector (403) thereby inducing negative pressure in the pressure chamber (405). The negative pressure in the pressure chamber (405) moves dialysate from the peritoneal cavity of the patient into the storage chamber (406) through check valve (408). At the same time as the storage chamber (406) is actuated under negative pressure, the enrichment module (411, see FIG. 4C) is also actuated under negative pressure by the pump such that a predetermined amount of an enrichment solution is withdrawn from an enrichment solution reservoir (412) though check valve (413) into the enrichment module (411).

In use during the inflow mode once the storage chamber (406) is full, the pump actuates the deformable diaphragm (420) located in the wall of the storage chamber (406) via the conduit connector (403) by transmitting fluid to the conduit connector (403) and thereby inducing positive pressure in the pressure chamber (405). The positive pressure in the pressure chamber (405) moves dialysate from the storage chamber (406) and check valve (408) closes preventing dialysate from returning to the peritoneal cavity before being treated to remove contaminants. Dialysate flows from the storage chamber (406) into the sorbent zone (407) through channel (416). The regenerated dialysate exiting from the sorbent zone (407) flows past a hydrophobic membrane (410) to remove any unwanted gas emitted during the dialysis operation. The degassed dialysate then flows past an enrichment module (411), a check valve (409) and exits the disposable housing via tube connector (415).

In the inflow mode, the pump also actuates the enrichment module (411) under positive pressure and check valve (413) closes. The enrichment module (411) dispenses a preselected amount of enrichment solution containing desired substances, such as electrolytes, osmotic agents, nutrients, medication and the like, into the dialysate through check valve (414). The dialysate is then returned to the peritoneal cavity via a check valve (409) and a tube connector (415).

Figure 5:
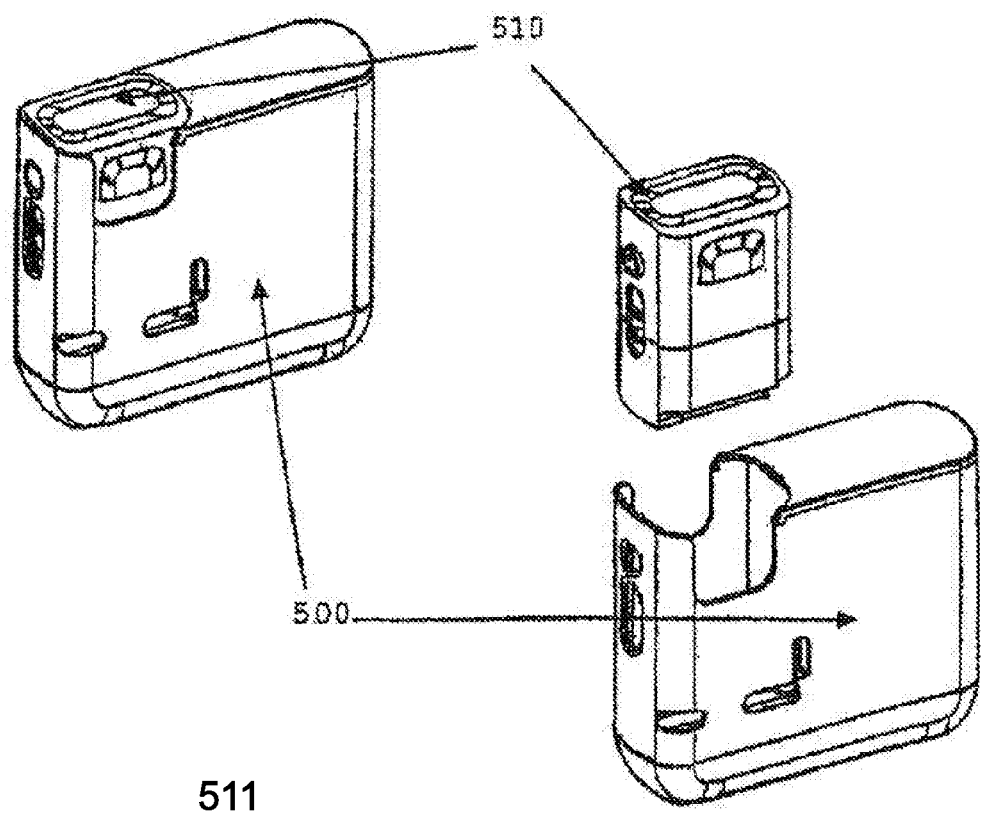
FIG. 5 is a perspective view of a prototype of one embodiment of the dialysis device disclosed herein.

Referring now to FIG. 5, there is shown a picture of a prototype of one embodiment of the entire flow system disclosed herein, with a disposable housing (500) and the control housing (510). The embodiment of FIG. 5 shows a kit comprising the dialysis device according to the present disclosure, together with instructions (511) for use.

Figure 6:
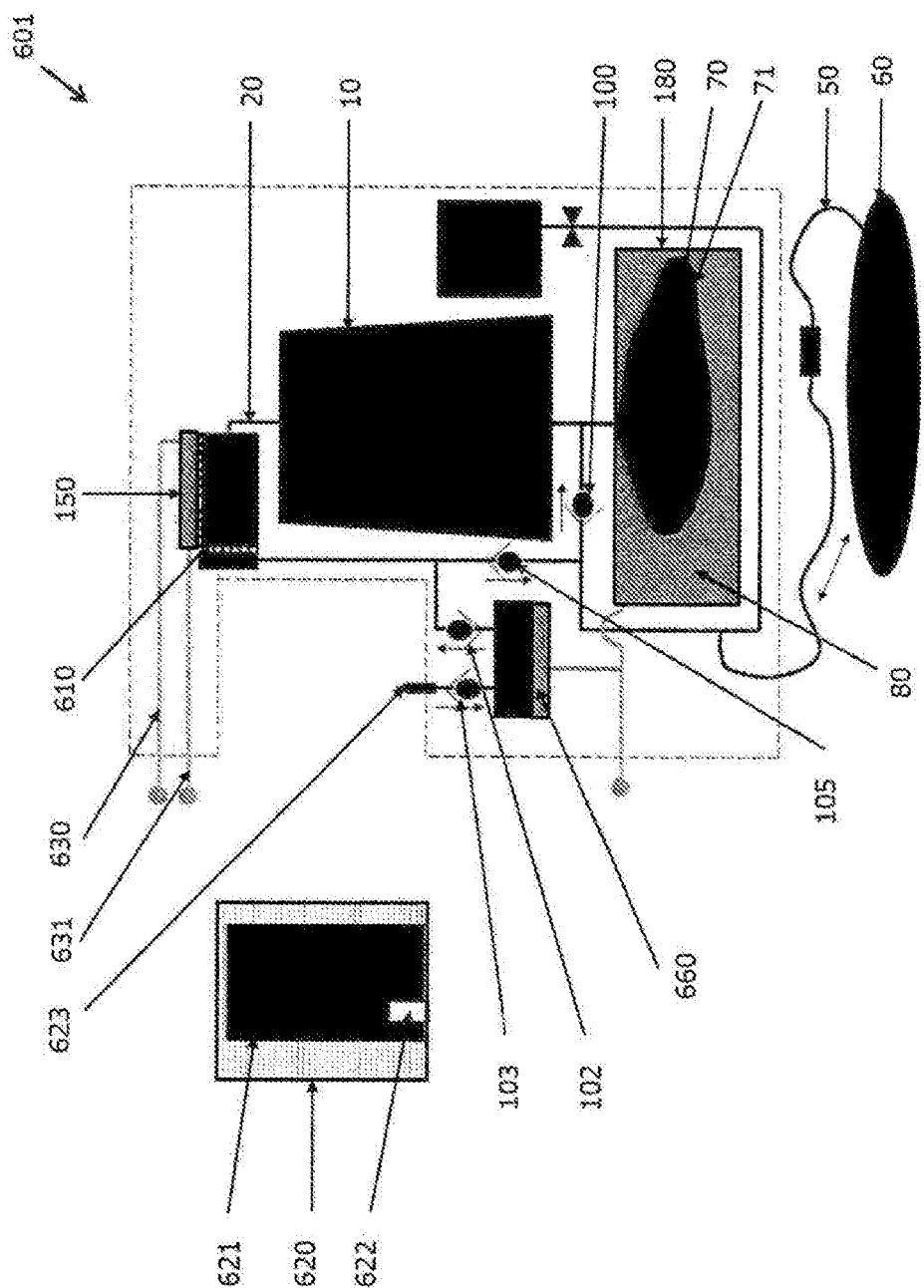
FIG. 6 is a schematic diagram of one embodiment of the disclosed disposable housing comprising a discrete additive dispensing means.

Referring to FIG. 6, there is shown one embodiment of a disposable housing (601) having a flow path in the form of conduit (20). The disposable housing (601) comprises a flexible dialysate tube (50) which is capable of being in fluid communication with the peritoneal cavity (60) and a conduit (20). The dialysis device further comprises a storage chamber (70) located in a rigid compartment (180). The storage chamber (70) comprises a deformable diaphragm (71) integrally formed in one of the walls of the storage chamber (70). The deformable diaphragm (71) is in fluid communication on one side with the dialysate conduit (20) and, on another opposite side, in fluid communication with a pressure chamber (80).

The pump (670) is configured to actuate the deformable diaphragm (71), by inducing a pressure change in the pressure chamber (80) which deforms the deformable diaphragm (71) and thereby moves dialysate within said dialysate conduit (20).

Check valves (100,102,103,105) are disposed along the conduit (20) and are configured to, in the outflow mode, allow the dialysate to flow from the peritoneal cavity (60) to the storage chamber (70), and in the inflow mode allow the dialysate to flow from the storage chamber (70) to said sorbent zone (110) for removal of contaminants therein, and further permit the dialysate substantially free of said contaminants to flow back to the peritoneal cavity (60).

The disposable housing is also provided with a discrete enrichment module (620), for dispensing a preselected amount of an enrichment solution into the dialysate. The enrichment module is not in fluid communication with the dialysate flow path in this figure. The enrichment module comprises an enrichment solution reservoir (621), a container in the form of a bag manufactured from a biocompatible material for holding the enrichment solution (not shown). The enrichment module (620) is provided with a connector (622) adapted for fluid communication with the dialysate conduit (20) of the disposable housing (601). The connector (622) is sealed prior to insertion into the disposable housing to maintain the sterility of the enrichment solution in the enrichment module (620). The disposable housing is provided with a male connector (623) of complementary configuration to the connector (622) located on the enrichment module (620). When in mating engagement (see FIG. 7) the male connector (623) serves to break the seal of the connector (622) to form a fluid connection between the enrichment reservoir (621) in the enrichment module (620) and the dialysate conduit (20) of the disposable housing (601).

The disposable housing (601) also comprises an enrichment pump (660) for adding a predetermined amount of enrichment solution to the dialysate conduit (20).

A degasser in the form of a hydrophobic membrane (150) is also located downstream of the sorbent zone (110). The external side of the hydrophobic membrane (150) is in fluid communication with air conduits (630 and 631).

A hydrophilic membrane (610) is disposed in the degasser compartment, in the dialysate flow path and directly downstream of the hydrophobic degasser membrane (150). The hydrophilic membrane (610) serves as a barrier to prevent gas, particles and bacteria contained in the dialysate exiting the sorbent zone (110) from reaching the peritoneal cavity (60). The membrane also produces a backpressure facilitating the venting of gas through the degasser membrane (150).

Figure 7:
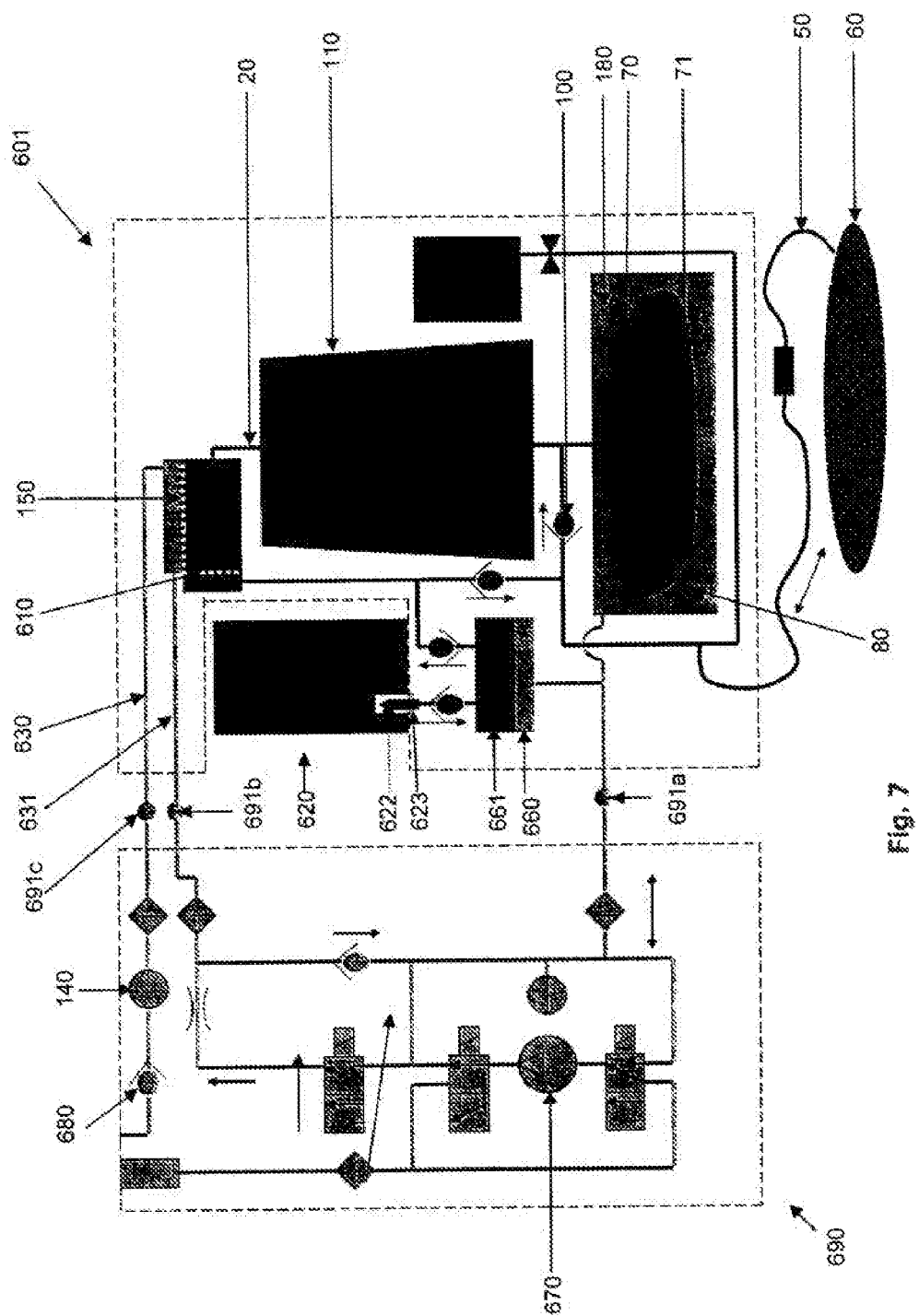
FIG. 7 is a schematic diagram of one embodiment of the disclosed dialysis device comprising a discrete additive dispensing means in locking engagement with a disposable housing in accordance with the disclosure.

Referring to FIG. 7, there is shown an embodiment of the disclosed dialysis device (700). The dialysis device comprises a disposable housing (601) having a flow path in the form of conduit (20), a controller in the form of a control housing (690) for controlling the operation of the disposable housing (601). The disposable housing (601) and control housing (690) comprise interface in the form of conduit connectors (691*a*, 691*b*, 691*c*) that connect the control housing (690) and the disposable housing (601). The disposable housing (601) and control housing (690) are brought into operative engagement when the conduit connectors are brought into locking engagement. The conduit (20) of the disposable housing (601) is fluidly sealed from the control housing (690) and conduit connectors (691*a*, 691*b*, 691*c*).

The dialysis device (700) comprises a flexible dialysate tube (50) which is capable of being in fluid communication with the peritoneal cavity (60) and a conduit (20). The dialysis device further comprises a storage chamber (70) located in a rigid compartment (180). The storage chamber (70) comprises a deformable diaphragm (71) integrally formed in one of the walls of the storage chamber (70). The deformable diaphragm (71) is in fluid communication on one side with the dialysate conduit (20) and, on another opposite side, in fluid communication with a pressure chamber (80). When the disposable housing (601) and control housing (690) are operably coupled to each other, the conduit connector (691*a*, 691*b*, 691*c*) fluidly couples the pressure chamber (80) of the disposable housing (601) to an air pump (670) located in the control housing (690).

The air pump (670) is configured to actuate the deformable diaphragm (71), by inducing a pressure change in the pressure chamber (80) which deforms the deformable diaphragm (71) and thereby moves dialysate within said dialysate conduit (20).

Check valves (100,102,103,105) are disposed along the conduit (20) and are configured to, in the outflow mode, allow the dialysate to flow from the peritoneal cavity (60) to the storage chamber (70), and in the inflow mode allow the dialysate to flow from the storage chamber (70) to said sorbent zone (110) for removal of contaminants therein, and further permit the dialysate substantially free of said contaminants to flow back to the peritoneal cavity (60).

In this figure the discrete enrichment module (620), is located in the disposable housing (601). The connector (622) of the enrichment module (620) is in mating engagement with the male connector (623) of the disposable housing to form a fluid connection between the enrichment reservoir (621) in the enrichment module (620) and the dialysate conduit (20) of the disposable housing (601).

The disposable housing (601) also comprises an enrichment pump (660) for adding a predetermined amount of enrichment solution to the dialysate conduit (20).

The enrichment pump (660) is a fixed displacement pump comprising a diaphragm (661) in fluid communication with the air pump (670). The air pump (670) exerts a positive or a negative air pressure to the diaphragm (661) of the enrichment pump (660) and the deformable diaphragm (71) of the storage chamber (70), functioning as pneumatic pump for cycling dialysate through the dialysate conduit (20) at the same time. On one side of the diaphragm (661) in the enrichment pump (660) is an air compartment which fluidly connects to the air pump (670), and the other side is the enrichment solution compartment connecting to the enrichment reservoir (621) reservoir via the mated connectors (622,623). When the enrichment solution compartment is subjected to negative pressure enrichment solution is drawn from the enrichment reservoir (621). When a positive pressure is applied to the air compartment, the enrichment solution is forced out of the enrichment pump (660) into the dialysate conduit (20).

A degasser in the form of a hydrophobic membrane (150) is also located downstream of the sorbent zone (110). The external side of the hydrophobic membrane (150) is in fluid communication with air conduits (630 and 631). In a normal dialysis operation, air conduit (630) is an outlet to the ammonia sensor (140) and air conduit (630) is in fluid communication with the air pump (670). During degassing, the air pump (670) in the control housing (690) exerts a negative pressure to remove any gas from the dialysate in the dialysate conduit (20). A check valve (680) prevents external air from entering air conduit (630).

A hydrophilic membrane filter (610) downstream of the hydrophobic membrane (150), prevents gas, particles and bacteria contained in the dialysate from reaching the peritoneal cavity (60). The membrane (610) also produces a backpressure facilitating the venting of gas through the hydrophobic membrane (150).

Figure 8A:
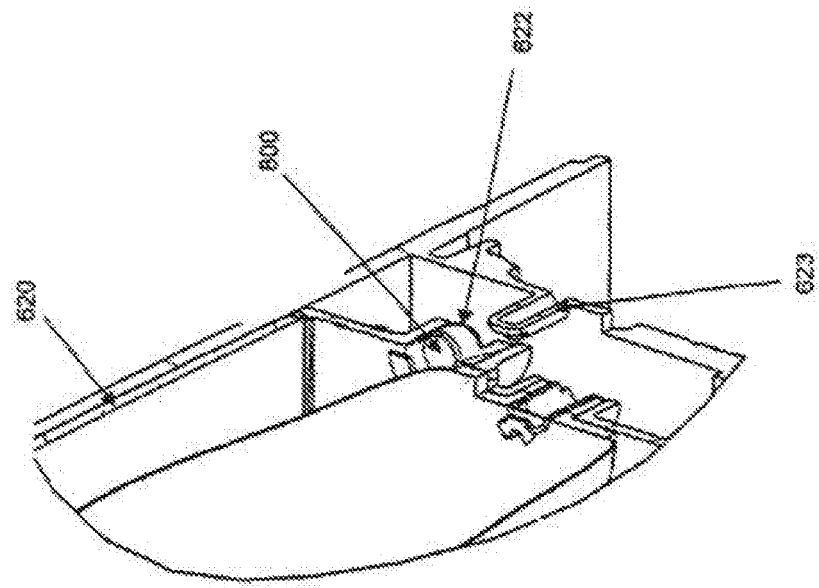
FIGS. 8A and 8B are cross sectional views of a sealed connector of the additive dispensing means in accordance with the disclosure.
Figure 8B:
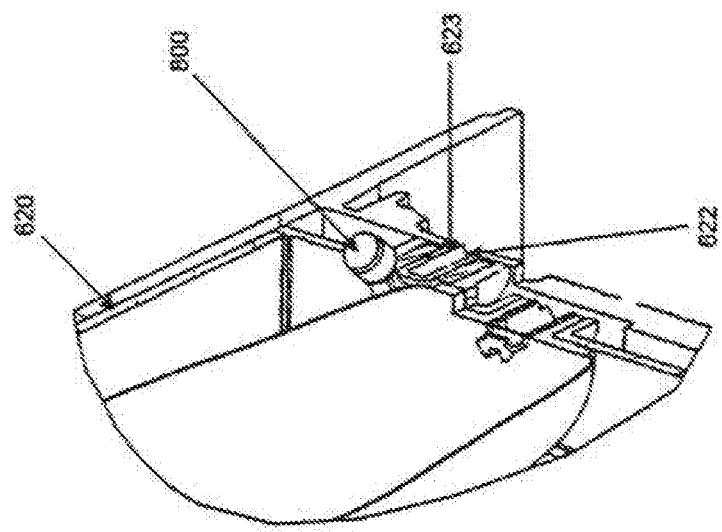

FIG. 8A and FIG. 8B show an embodiment of a sealed connector (622) in accordance with the present invention. The connector (622) on the enrichment module (620) is provided with a plug (800) that can be dislodged by the connector (623) located on the disposable housing (601). In FIG. 8B, the connector (622) on the enrichment module is brought into mating engagement with the connector (623) on the disposable housing (601) to dislodge the plug (800).

FIG. 9A and FIG. 9B show an embodiment of a sealed connector (622) in accordance with the present invention. The connector (622) on the enrichment module (620) is provided with a plug (800) that can be pierced by the connector (623) located on the disposable housing (601). In FIG. 8B, the connector (622) on the enrichment module is brought into mating engagement with the connector (623) on the disposable housing (601) to pierce the plug (800).

FIG. 10A and FIG. 10B show the embodiment of a sealed connector of FIG. 9A and FIG. 9B. The connector (622) on the enrichment module (620) is provided with a plug (800) that can be pierced by the connector (623) located on the disposable housing (601). In FIG. 10B, the connector (622) on the enrichment module is brought into mating engagement with the connector (623) on the disposable housing (601) to pierce the plug (800). The enrichment module is a rigid container for holding the additive solution, comprising a sponge (1001) located at an end of the container in communication with a connector (622). The sponge facilitates delivery of the enrichment solution from the enrichment reservoir (621) to the dialysate conduit (20).

Figure 11:
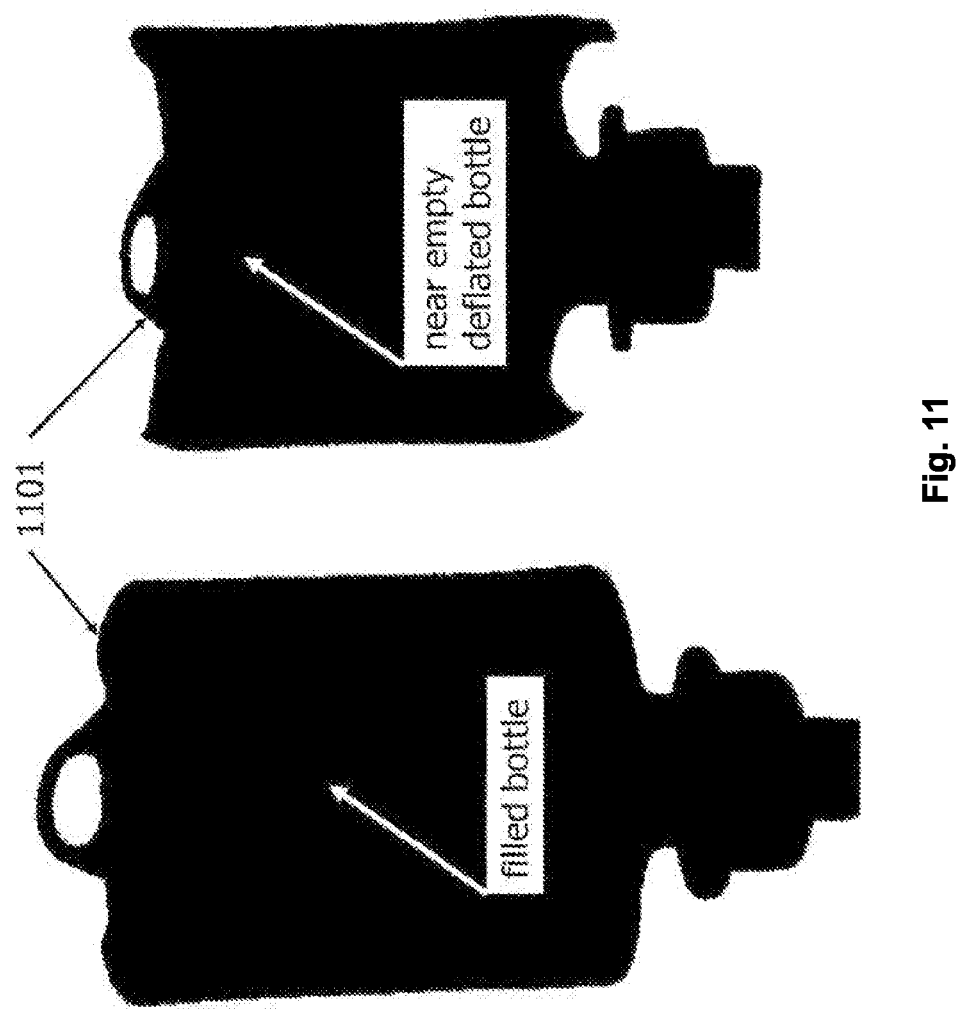
FIG. 11 is a cross sectional view of an embodiment of an additive dispensing means in accordance with the disclosure.

FIG. 11 shows another embodiment of a container in the enrichment module (620). In this figure the container is in the form of a resiliently deformable bottle (1101). The bottle on the left hand side is full of enrichment solution. The bottle on the right hand side of the figure is depleted.

Figure 12A:
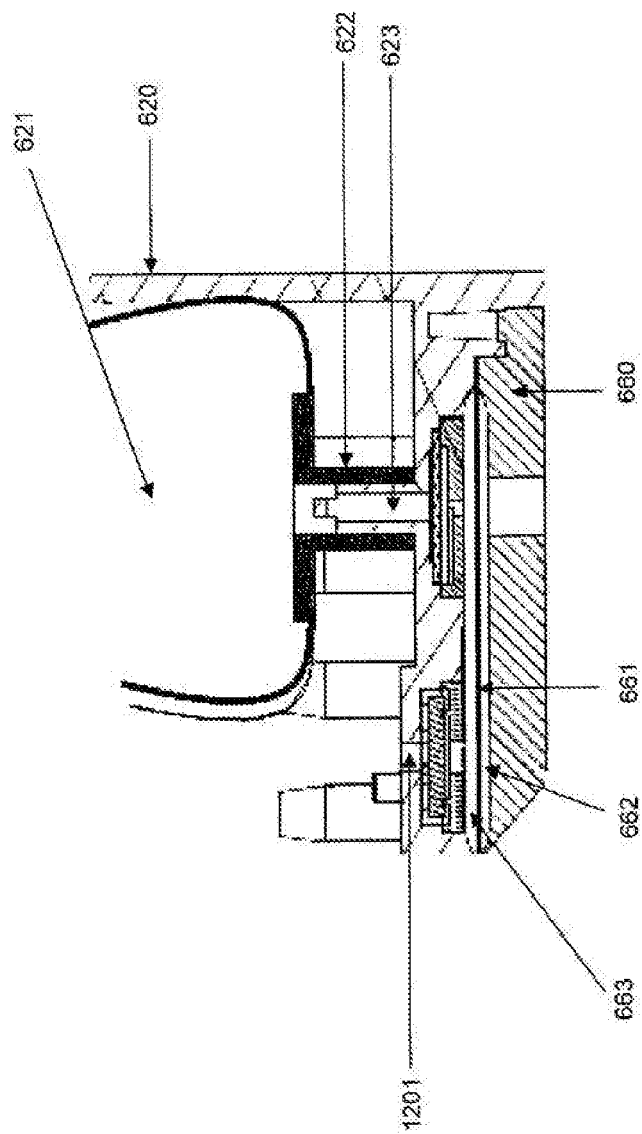

FIG. 12A shows a cross-sectional view of the enrichment pump (660). The enrichment module (620) comprises an enrichment reservoir (621) in fluid communication with the enrichment pump (660) via the mated connectors (622 and 623). The enrichment pump (660) is provided with a diaphragm (661) which defines an air chamber (662) in fluid communication with the air pump (not shown) and an enrichment solution chamber (663) in fluid communication with the enrichment reservoir (621).

Figure 12B:
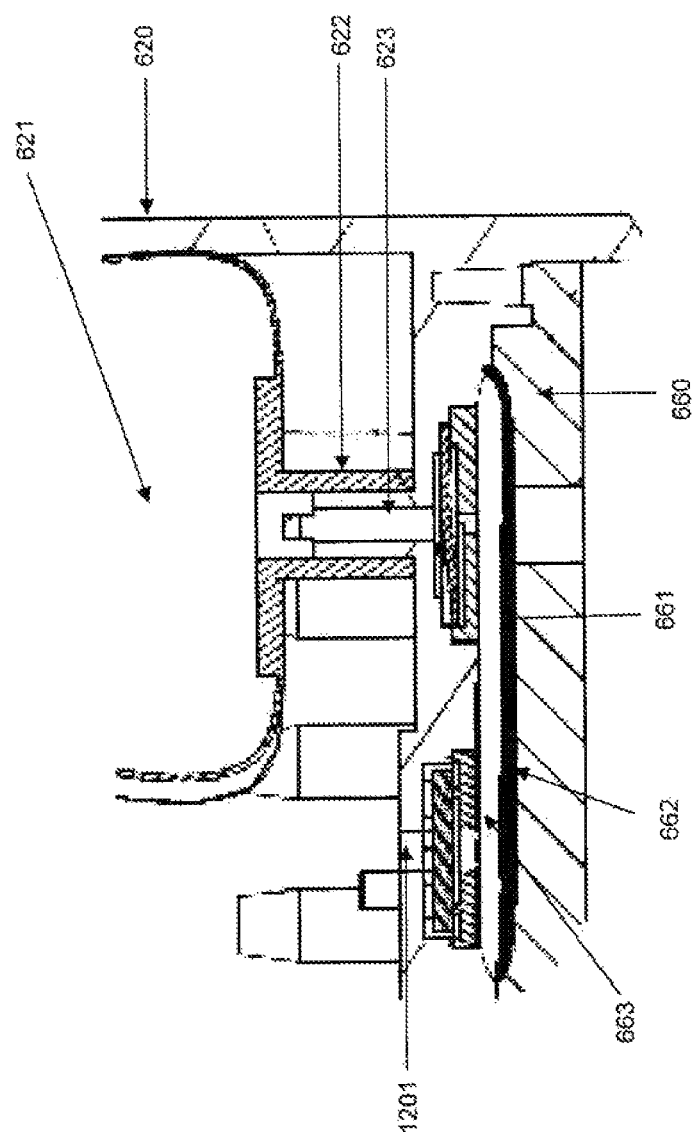

FIG. 12B shows a close up view of FIG. 12A in an outflow cycle. When the air pump exerts a negative pressure beyond 50 mmHg, in the dialysate outflow cycle, enrichment solution is drawn from the enrichment reservoir (621) into the enrichment solution chamber (663) of the enrichment pump (660).

FIG. 12C shows the enrichment pump (660) in an inflow cycle. In the inflow cycle when a positive pressure greater than 200 mmHg is exerted in the air chamber (662), the enrichment solution chamber (663) will be emptied and a fixed volume of enrichment solution, VEP, will flow to and merge with the dialysate in the dialysate conduit via outlet (1201).

Figure 13:
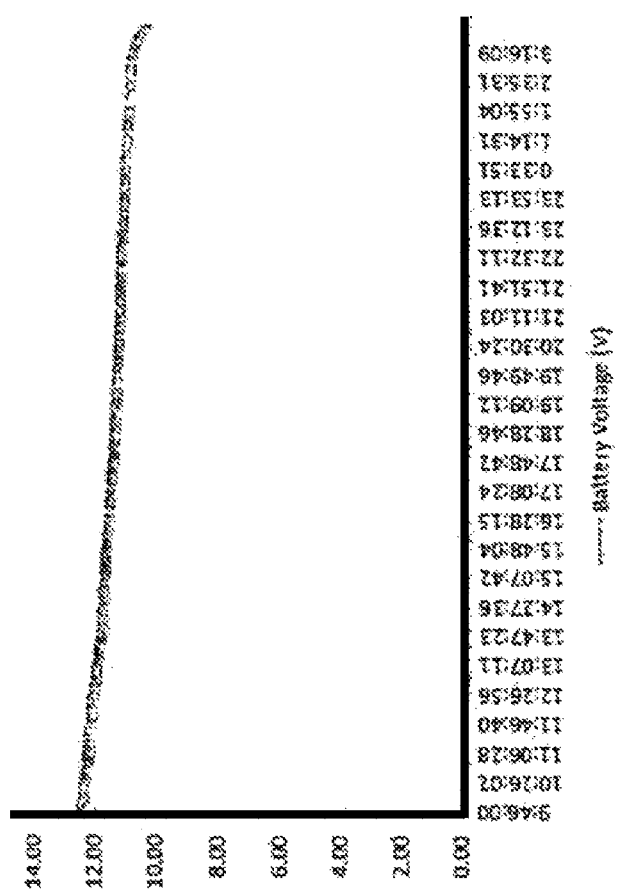
FIG. 13 is a graphic representation of the voltage drop of a rechargeable battery versus dialysis time in a dialysis device in accordance with the disclosure.
Figure 14:
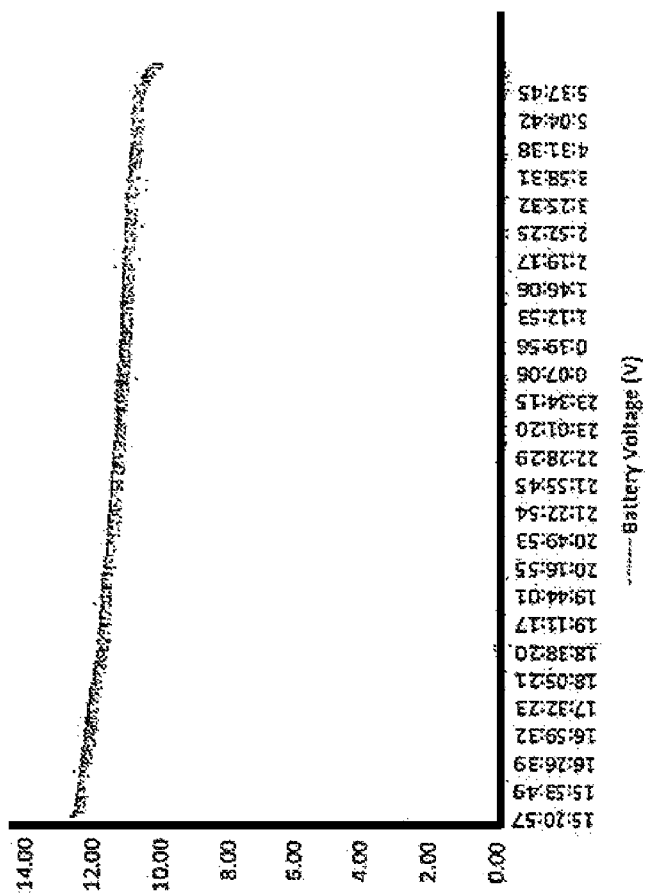
FIG. 14 is a graphic representation of the voltage drop of a rechargeable battery versus dialysis time with constant pumping in a device in accordance with the disclosure.

FIG. 13 and FIG. 14 show the results of battery tests on a dialysis device in accordance with the disclosure. The purpose of the experiment was to determine the minimum capacity of the battery that is needed to support the operation of a high capacity dialysis cartridge for at least 12 hours. Based on an average power consumption of 153 mA of the system, for a 12 hour operation, the minimum battery capacity needed would be at least 1836 mAh. Thus, to retain at least 80% of the battery capacity over a year, the minimum battery needed will be 2203 mAH. This is according to the retentive specifications of the battery, where the battery capacity will drop to 80% of its overall capacity when its operation cycle is more than 300 cycles (1836 mAh×120%). To determine the actual usage duration for the system, 2 tests were performed using an 11.1V, 2250 mAH, Lithium Polymer battery.

Test #1:

Taking a representative operation scenario for a normal flow control, where the pump is being turned ON and OFF to maintain at either 400 mmHg (Inflow) or −100 mmHg (Outflow), without a relaxation of the pressure, the result showed that a 2250 mAh capacity battery was able to support the mentioned operation for 18 Hrs before it was shut down by the firmware at 10.5V. FIG. 13 shows the graph showing the voltage drop of the battery versus the operation time in this experiment.

Test #2:

In the second test, assuming the worst case scenario that the pump is constantly ON for the whole inflow and outflow cycle operation, the results show that the battery can last for 14.5 Hrs before it was shut down by the firmware at 10.5V. Below is the graph showing the voltage drop of the battery versus the operation time in this experiment.

Figure 15A:
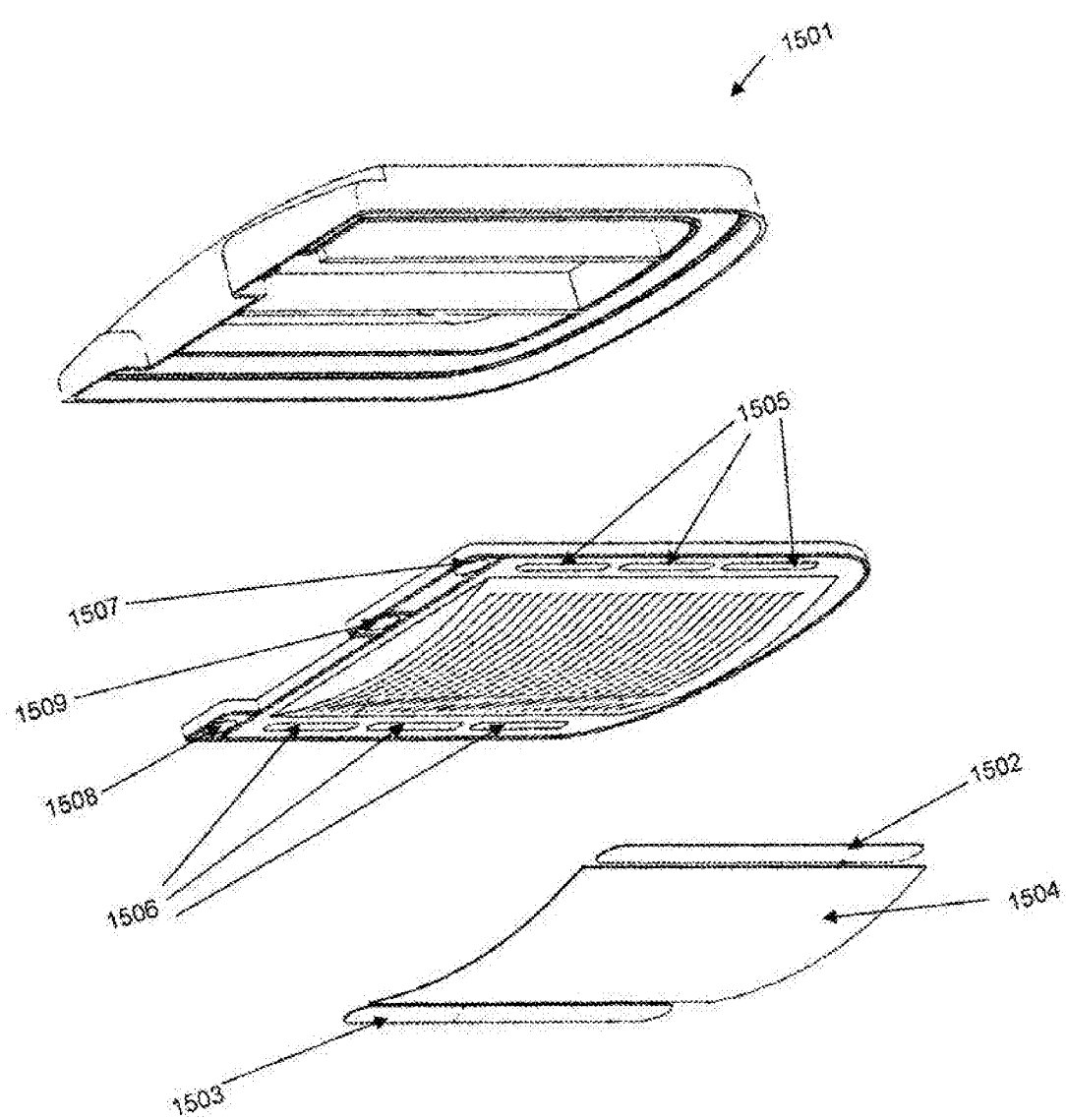
FIG. 15A is an exploded view of embodiment of a degasser in a device in accordance with the disclosure.

FIG. 15A shows an exploded view of a degasser (1501) in accordance with the disclosure. The degasser comprises a gas vent means in the form of two hydrophobic membranes (1502) and (1503). The hydrophobic membranes are arranged in parallel on either side of a hydrophilic membrane (1504). Each hydrophobic membrane (1502 and 1503) is located adjacent to air vents (1505 and 1506). The degasser is also provided with air inlets/outlets (1507 and 1508) and a dialysate outlet (1509). The hydrophilic membrane is curved to facilitate the flow of gas in the dialysate to the hydrophobic membranes and subsequently the air vents to remove gas from the dialysate in the dialysate conduit of the dialysis device. In use a 4 micro paper filter seals the top of the sorbent zone in the dialysis device and is covered by the degasser. The hydrophilic membrane is located adjacent to the paper filter by a spacer (not shown). The hydrophilic membrane reduces sorbent powder leakage from the sorbent zone and paper filter and also acts as a bacterial filter.

Figure 15B:
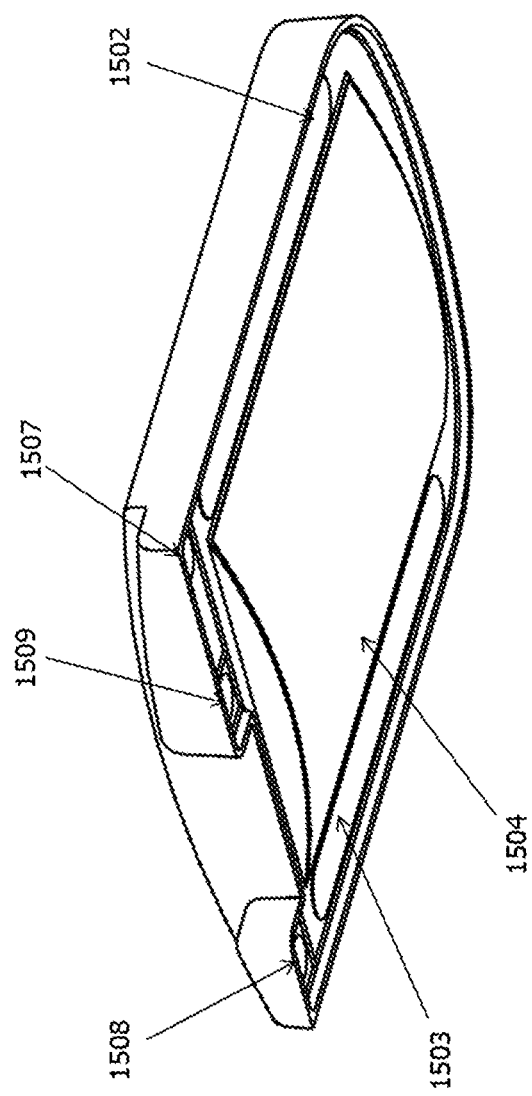
FIG. 15B is an embodiment of a degasser in a device in accordance with the disclosure.

Referring to FIG. 15B, in a normal dialysis operation, a first air outlet (1507) is in fluid communication with an ammonia sensor and a second air outlet (1508) is in fluid communication with a degassing exhaust via another connecting air-port (not shown). When detecting for ammonia gas presence in the case of sorbent cartridge exhaustion, atmospheric air flows through a throttle valve, or any stable flow constrained valves, in the controller, allowing a controlled amount of air to flow through the first air outlet (1507), to an air conduit above the hydrophobic membranes, and flow out from the other end of the air conduit to the second air outlet (1508), and circulate to an ammonia sensor in the controller. During degassing, the air pump in the controller exerts a negative pressure to remove any gas, in particular $CO_2$, in the air conduit via the first air outlet (1507) back to an exhaust in the controller.

Figure 16:
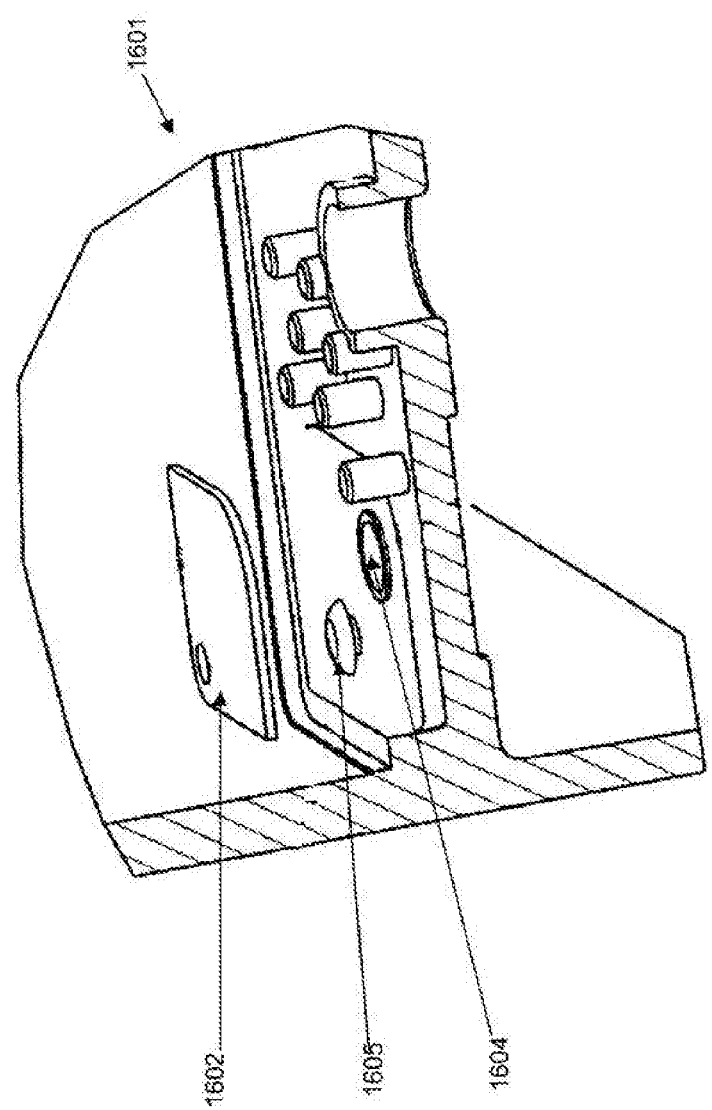
FIG. 16 is an embodiment of a fibrin trap in a device in accordance with the disclosure.

Referring to FIG. 16, an exploded view of a fibrin trap (1601) is shown. During dialysis, it is possible that dialysate will contain some small amount of fibrin. The trap comprises an inlet valve (1602) and a filter (not shown) located opposite the inlet valve (1602). The inlet valve is in the form of a resiliently deformable disk hinged on a stud (1605) such that the hinge is located away from the dialysate flow into the trap and thus will not catch on any fibrin present in the dialysate. In use the dialysate enters the trap through an inlet (1604) and passes through the disk valve (1602). The disk valve is located on a stud (1605). During an outflow mode, the disk valve (1602) is closed against the inlet (1604) preventing the flow of dialysate from the sorbent zone to the patient. The dialysate that enters the sorbent zone may comprise fibrin. The fibrin is prevented from entering the sorbent zone by the filter (1603) and is therefore retained in the trap (1601).

Figures 17A, 17B:
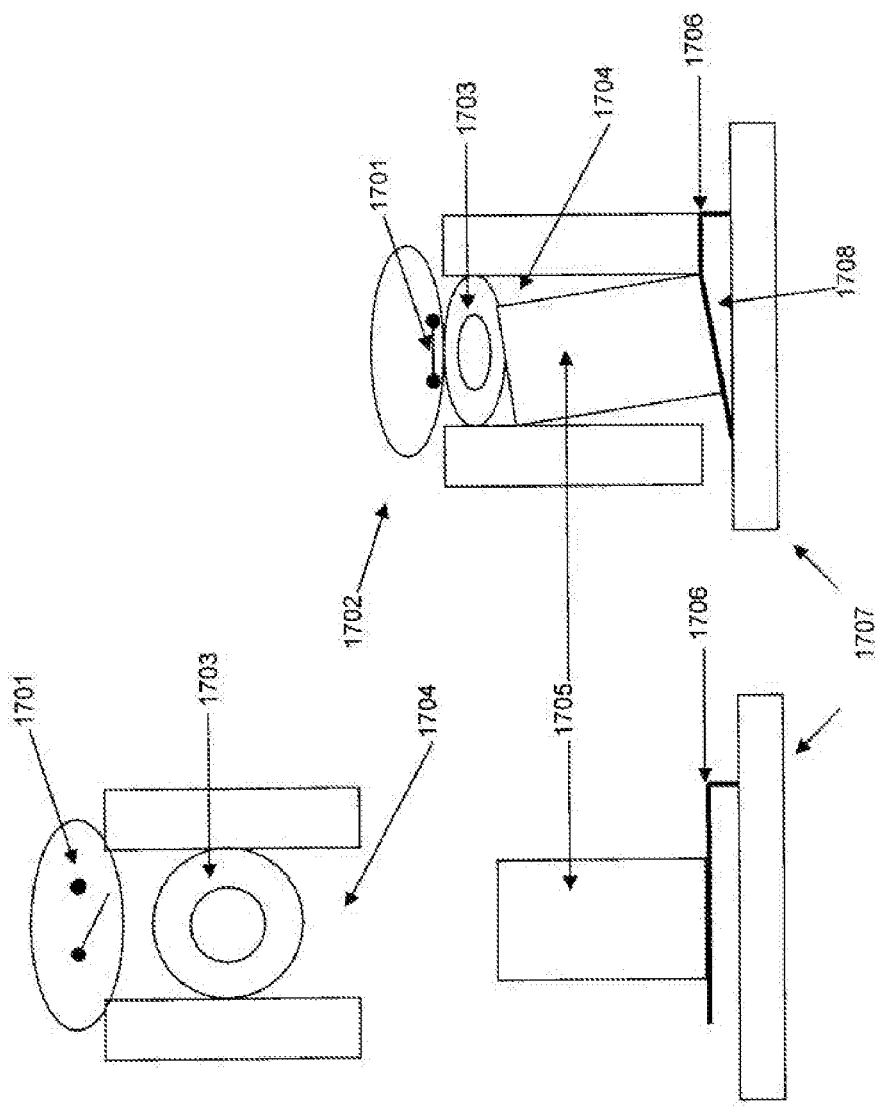
FIGS. 17A and 17B show an embodiment of a power-connecting switch in accordance with the disclosure.

FIG. 17A shows a power-connecting switch in accordance with an embodiment of an invention. The switch (1701) is located in the controller (1702). The switch is in an open condition when the controller (1702) is not coupled to a disposable housing. A resiliently deformable material, in the form of a rubber tube (1703), is located in a channel (1704), immediately adjacent to the switch (1701).

A pin (1705) is located on a breakable frame (1706) on the disposable housing (1707), which is of complementary configuration to the channel (1704) located on the controller (1702). When the disposable housing and controller are coupled together, the pin (1705) is received in the channel (1704) and the frame is deformed and broken (1708) by the controller (1702) (FIG. 17B).

The pin (1705) when located in the channel (1704) exerts a positive compressing force on the rubber tube (1703) which closes the switch (1701). The frame continues to urge the pin toward the rubber tubing to actuate the switch (1701) into a closed condition (FIG. 17B). The switch (1701) now electrically connects the battery (not shown) to the controller to permit the dialysis device to be used by a patient. The fractured frame (1706) can no longer hold the pin (1705) rigidly upright for the pin (1705) to get inserted into the channel (1704) on the controller (1702) again.

Applications

It is an advantage of the device that as the flow path is fluidly sealed from the controller the sterility of the device can be maintained by daily disposal of disposable housing.

It is a further advantage of the dialysis device that a single connector between the disposable housing and controller is required, thus reducing the complexity of setting the device up for operation.

It is a further advantage that the size of the dialysis device according to the disclosure can be significantly reduced relative to other dialysis devices.

It is a further advantage that the device according to the disclosure is energy efficient.

It is an advantage of the device according to the disclosure that as the fluid displacement means is integrally formed with a wall of the storage chamber this permits the pumping mechanism of the dialysis device to be shared by the storage chamber thereby permitting a reduction in the size of the disposable housing. This is further advantageous as it permits the construction of a more portable and unobtrusive device to be used by a patient.

It is a further advantage that the connector between the disposable housing and the controller is fluidly sealed to prevent biological or chemical contamination of the device. It is an advantage of the device that, as the flow path is fluidly sealed from the controller, the risk of biological and/or chemical contamination of the dialysate by the controller is significantly reduced.

It is a further advantage of the device that as only one pump and only one interface connector is required this reduces the requirement for additional pumps and connections and thus results in a significant reduction in the size of the dialysis device relative to known dialysis devices.

It is a further advantage of the device of the disclosure that as only one pump is required to activate a storage chamber, an additive dispensing means and a gas vent means, this further permits miniaturization of the device and enhances portability and energy efficiency.

It is a further advantage that as only one pump is required to activate the storage chamber, the additive dispensing means and the gas vent means, there is a significant reduction in the complexity of the device, which results in a decrease in manufacturing costs relative to known dialysis devices.

It is a further advantage of the device that the pressure sensor can also be used to measure a patient's intraperitoneal pressure, without additional pressure sensors.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

What is claimed is:

1. A dialysis device, comprising:
a disposable housing having a dialysate flow path along which dialysate received from a patient is subjected to contaminant removal when in operation, wherein said disposable housing comprises a storage chamber in fluid communication with the dialysate flow path for storing the dialysate therein for contaminant removal;
a controller for controlling the operation of said disposable housing;
an interface capable of operably coupling the controller and the disposable housing to enable the contaminant removal from the dialysate;
a fluid displacement structure, comprising a deformable diaphragm integrally formed with at least one wall of the storage chamber, and configured to move the dialysate along the dialysate flow path; and
a single pump configured to actuate the deformable diaphragm,
wherein the flow path is fluidly sealed from the controller and the interface, and
wherein the single pump is the only pump included in the dialysis device.

2. The dialysis device as claimed in claim 1, comprising a single pressure sensor to trigger the reversal of the pump from an outflow mode to an inflow mode, when the storage chamber is detected to be filled with dialysate, and from the inflow mode to the outflow mode, when the storage chamber is detected to be emptied of dialysate.

3. The dialysis device as claimed in claim 1, wherein the dialysis device is wearable.

4. The dialysis device as claimed in claim 1, wherein said deformable diaphragm is in fluid contact on one side with the dialysate flow path and, on another opposite side, in contact with a pressure chamber that is capable of receiving fluid therein.

5. The dialysis device as claimed in claim 4, wherein the deformable diaphragm is disposed in a rigid member in the disposable housing.

6. The dialysis device as claimed in claim 1, wherein the device is powered by a battery.

7. The dialysis device as claimed in claim 6, wherein the battery is a rechargeable battery, optionally wherein the rechargeable battery is a lithium polymer battery.

8. The dialysis device as claimed in claim 1, comprising an ammonia sensor configured to detect ammonia present in said dialysate.

9. The dialysis device as claimed in claim 8, wherein the ammonia sensor is disposed in the disposable housing.

10. The dialysis device as claimed in claim 8, wherein the ammonia sensor is configured to detect ammonia or ammonium ions.

11. The dialysis device as claimed in claim 8, wherein the ammonia sensor comprises a material which changes color in the presence of ammonia.

12. The dialysis device as claimed in claim 8, wherein the ammonia sensor comprises an ammonia-sensitive membrane.

13. The dialysis device as claimed in claim 1, wherein said disposable housing comprises a sorbent zone in fluid communication with the dialysate flow path for removing contaminants in the dialysate.

14. The dialysis device as claimed in claim 13, wherein the flow path comprises a fibrin trap located upstream of the sorbent zone.

15. The dialysis device as claimed in claim 13, wherein said storage chamber is upstream of said sorbent zone.

16. The dialysis device as claimed in claim 13, wherein said disposable housing further comprises valve means disposed along the dialysate flow path configured to control the direction of movement of the dialysate relative to the sorbent zone and storage chamber.

17. The dialysis device as claimed in claim 16, wherein said valve means is operative by the flow direction of dialysate along said flow path.

18. The dialysis device as claimed in claim 16, the controller further comprising an actuator for actuating said fluid displacement member and said valve means when said controller is connected to the disposable housing by said interface.

19. A kit comprising the dialysis device of claim 1, together with instructions for use.

\* \* \* \* \*